(12) United States Patent
Pak

(10) Patent No.: US 8,071,547 B2
(45) Date of Patent: Dec. 6, 2011

(54) COMPOSITIONS OF ALPHA-FETOPROTEIN AND INDUCERS OF APOPTOSIS FOR THE TREATMENT OF CANCER

(75) Inventor: Vladimir Pak, Toronto (CA)

(73) Assignee: Constab Pharmaceutical, Inc., Toronto, Ontario (CA)

( * ) Notice: Subject to any disclaimer, the term of this patent is extended or adjusted under 35 U.S.C. 154(b) by 133 days.

(21) Appl. No.: 12/093,842

(22) PCT Filed: Nov. 15, 2006

(86) PCT No.: PCT/CA2006/001867
§ 371 (c)(1),
(2), (4) Date: Aug. 18, 2008

(87) PCT Pub. No.: WO2007/056852
PCT Pub. Date: May 24, 2007

(65) Prior Publication Data
US 2008/0318840 A1      Dec. 25, 2008

(51) Int. Cl.
*A61K 38/00*    (2006.01)
*A01N 45/00*    (2006.01)
*A61P 35/00*    (2006.01)

(52) U.S. Cl. ....... 514/15.3; 514/19.3; 514/169; 514/313

(58) Field of Classification Search .................. None
See application file for complete search history.

(56) References Cited

U.S. PATENT DOCUMENTS

| | | | |
|---|---|---|---|
| 6,534,479 B1 | 3/2003 | Murgita | |
| 6,599,507 B2 * | 7/2003 | Strelchenok | 424/193.1 |
| 6,630,445 B2 | 10/2003 | Murgita | |
| 6,878,688 B2 | 4/2005 | Pak et al. | |
| 2002/0051778 A1 * | 5/2002 | Pak et al. | 424/94.63 |
| 2003/0186945 A1 | 10/2003 | Pezzuto et al. | |
| 2009/0062227 A1 | 3/2009 | Schonthal et al. | |
| 2009/0233849 A1 * | 9/2009 | Benevolensky et al. | 514/12 |

OTHER PUBLICATIONS

Copado et al., J Protein Chem. May 1999;18(4):413-424.*
NCBI Accession NP_999482, alpha-fetoprotein [*Sus scrofa*] May 20, 2004.*
Tempero, M., ed., et al. "Everyone's Guide to Cancer Therapy." 4th Ed. Andrews McMeel Publishing. Jan. 20, 2003: 174.
Haouzi, D., et al. "Mitochondrial permeability transition as a novel principle of hepatorenal toxicity in vivo." Apoptosis. Oct. 2002;7(5):395-405.
Pak, V. "The Use of AFP—Complexes to Induce Apoptosis in Cancer Cells." Open Cancer J. 2008;2:12-14.
Obatomi, D.K., et al. "Biochemistry and toxicology of the diterpenoid glycoside atractyloside." Food Chem Toxicol. Apr. 1998,36(4):335-46.
Ahn, Y.S., et al. "Selective extraction of alkaline phosphatase and 5'-nucleotidase from milk fat globule membranes by a single phase n-butanol procedure." Prep Biochem. Aug. 1993;23(3):409-19. [Abstract].
Nath, R., et al. "Thapsigargin induces apoptosis in SH-SY5Y neuroblastoma cells and cerebrocortical cultures." Biochem Mol Biol Int. Sep. 1997;43(1):197-205.
D'Ancona, S., et al. "Effects of atractylosides and bongkrekic acid, inhibitors of mitochondrial adenine nucleotide carrier, on growth and structure of tumor cells (F 10) in vitro." Fitoterapia. 1989;60(6):509-517.
Luft, A.J., et al. "Distribution of alpha-fetoprotein in fetal plasma and in amniotic and allantoic fluids of the pig." J Reprod Fertil. Mar. 1984;70(2):605-7.
Mizejewski, G.J. "Biological role of alpha-fetoprotein in cancer: prospects for anticancer therapy." Expert Rev Anticancer Ther. Dec. 2002;2(6):709-35.
Thapsigargin. Product Information Sheet. Sigma-Aldrich. Accessed Mar. 29, 2001. <http://http://www.sigmaaldrich.com/etc/medialib/docs/Sigma/Product_Information_Sheet/t9033pis.Par.0001.File.tmp/t9033pis.pdf>, (2009).
Darling, R. J., et al. "Glycosylation of erythropoietin affects receptor binding kinetics: role of electrostatic interactions." Biochemistry. Dec. 10, 2002;41(49):14524-31 [Abstract].
Dollinger, M., et al. Everyone's Guide to Cancer Therapy: How Cancer is Diagnosed, Treated, and Managed Day to Day, Fourth Edition, p. 174, (2002).
Fulda, S., et al. "Activation of mitochondria and release of mitochondrial apoptogenic factors by betulinic acid." J Biol Chem. Dec. 18, 1998;273(51):33942-8.
Fulda, S., et al. "Betulinic acid triggers CD95 (APO-1/Fas)- and p53-independent apoptosis via activation of caspases in neuroectodermal tumors." Cancer Res. Nov. 1, 1997;57(21):4956-64.
Lutsenko, S. V., et al. "Antitumor activity of alpha fetoprotein and epidermal growth factor conjugates in vitro and in vivo." Tumour Biol. Nov.-Dec. 2000;21(6):367-74.
Mizejewski, G. J. "Alpha-fetoprotein structure and function: relevance to isoforms, epitopes, and conformational variants." Exp Biol Med (Maywood). May 2001;226(5):377-408.
Mizejewski, G. J. "Biological roles of alpha-fetoprotein during pregnancy and perinatal development." Exp Biol Med (Maywood). Jun. 2004;229(6):439-63.

(Continued)

*Primary Examiner* — Daniel C Gamett
(74) *Attorney, Agent, or Firm* — Dann Dorfman Herrell & Skillman; Kathleen D. Rigaut

(57) ABSTRACT

The invention relates to novel compositions comprising alpha-fetoprotein (AFP) and methods for preventing, treating or inhibiting a malignant neoplasm expressing an alpha-fetoprotein receptor (AFPR) with or without multidrug resistance. Compositions comprising a non-covalent complex of an exogenous AFP, and at least one apoptosis-inducing agent selected from the group comprising mitochondrial membrane permeabilizing agents, mitochondrial pore opening inducing agents, ionophores, caspase 9 activators, caspase 3 activators and retinoids, are provided, wherein the at least one apoptosis-inducing agent reversibly binds to the exogenous AFP. The invention also provides for a process for butanol extraction of porcine alpha-fetoprotein obtained from blood and amniotic fluid extracted during early embryogenesis.

23 Claims, 7 Drawing Sheets

OTHER PUBLICATIONS

Nishi, S., et al. "Immunological and chemical correlation between alpha-fetoproteins from human and several mammalian species." Ann N Y Acad Sci. Aug. 22, 1975;259:109-18 [Abstract].

Semenkova, L., et al. "Alpha-fetoprotein positively regulates cytochrome c-mediated caspase activation and apoptosome complex formation." Eur J Biochem. Nov. 2003;270(21):4388-99.

Sotnichenko, A. I., et al. "Water-soluble 2,3,7,8-tetrachlorodibenzo—dioxin complex with human α-fetoprotein: properties, toxicity in vivo and antitumor activity in vitro." FEBS Letters. 1995 450(1): 49-51.

Tsuboi, S., et al. "High level of expression of alpha-fetoprotein receptor in gastric cancers." Tumour Biol. 2006;27 (6):283-8. Epub Oct. 6, 2006.

Van Oers, N. S. C., et al. "Isolation and characterization of a distinct immunoregulatory isoform of alpha-fetoprotein produced by the normal fetus." J Exp Med. Sep. 1, 1989;170(3):811-25.

* cited by examiner

Before Treatment

After Treatment

Before Treatment　　　　　　After Treatment

COMPOSITIONS OF ALPHA-FETOPROTEIN AND INDUCERS OF APOPTOSIS FOR THE TREATMENT OF CANCER

The present application is a §371 application of PCT/CA2006/001867 filed 15 Nov. 2006 which in turn claims priority from U.S. application Ser. No. 11/274,906, the contents of each being incorporated herein by reference as though set forth in full.

FIELD OF INVENTION

The present invention relates to the field of medicine, oncology in particular. The invention provides novel compositions and methods for treating, preventing and inhibiting malignant cell proliferation in mammals comprising AFP bound to an apoptosis inducer. The invention also provides for a process for butanol extraction of porcine alpha-fetoprotein obtained from blood and amniotic fluid extracted during early embryogenesis.

BACKGROUND OF THE INVENTION

Alpha-fetoprotein (AFP) is a major transport protein in the fetus, acting as a shuttle and having a halflife of 3-5 days (Mizejewski, G. J., in "AFP and Congenital Disorders", pp. 5-34, Academic Press, Orlando, 1985; Abelev, G I, Alpha-fetoprotein: 25 years of study, Tumor Biology, 10:63-74; 1989). Expression of AFP is tightly regulated during development such that detectable levels of AFP expression are largely dependent on the developmental stage. Studies have established that AFP acts as a growth regulator during both ontogenic growth and tumour progression. Due to expression of AFP during development and tumourigenesis, AFP is referred to as an oncofetal antigen.

AFP is a glycoprotein belonging to the albuminoid gene superfamily, of which albumin is also a member. The molecular weight of AFP can vary from 64,000 to 72,000 daltons depending on the source, developmental stage and the method used for its purification. Associated percentage of carbohydrate varies from 3% to 5% again depending on the source and developmental stage.

AFP appears to be present in two basic molecular forms: 1) an unbound form, and 2) a bound form in which AFP is complexed to various ligands (e.g. fatty acids, estrogens, phytosteroids). However, variant forms of AFP have been identified. Different conformations (holoforms) of bound AFP exist which are dependent on the nature and concentration of the bound ligand(s). Molecular variants of Human AFP (HAFP) have been identified wherein the variations are attributed to carbohydrate microheterogeneity (i.e. different carbohydrate moieties bind at the site of glycoslation on HAFP) as well as due to differences in isoelectric points (Keel, B. A., et al., CRC Press; vol 2, 24-31, 1989; Mizejewski, G. J., Exp. Biol. Med. 226(5):377-408, 2001; Morinaga, T. et al., Proc. Natl. Acad. Sci. USA, 80(15):4604-8, 1983; Parker, M. H. et al., Purification and characterization of a recombinant version of human AFP expressed in the milk of transgenic goats, Protein Expression and Purification, 38:177-183, 2004). Genetic variants of HAFP have been detected that are attributed to developmental phase-specific expression of HAFP mRNA.

Mizejewski G. J. et al. (Tumour Biol. 7(1): 19-36, 1986) describe the cyclic physiology of AFP as the "developmental clock". The authors note that the structure and function of AFP changes throughout the course of development where the protein is expressed in fluctuating levels during fetal development and expression levels decline to negligible levels post-naturally, having a normal adult serum concentration of less than 50 ng/mL (Ruoslahti and Seppala, Int. J. Cancer 8:374-378, 1971). However, AFP plasma levels can be one thousand-fold higher in individuals with various cancers (Ruoslahti and Seppala, Adv. Cancer Res. 29:275-310, 1979). In addition, a number of cancers express high levels of AFP receptors on their cell surfaces (Uriel, J. et al., in "Biological Activities of AFP", CRC Press, 1987, Boca Raton, Fla., vol. 2, pp. 104-117; Moro, R., in "Biological Activities of AFP", CRC Press, 1987, Boca Raton, Fla., vol. 2, pp. 120-127). Therefore, in humans, AFP functions as a tumor marker in addition to being a fetal defect marker during embryogenesis.

Various chemical preparations, such as alkylating agents, antimetabolites, alkaloids, antibiotics, hormones and immunomodulators, known in the prior art are used to treat cancer. However, these preparations do not specifically target tumor cells resulting in what is referred to as "bystander effect", where normal, non-tumour cells are also susceptible to the anti-cancer agent. The overexpression of HAFP receptors (HAFPR) on the surface of malignant cells, compared to negligible expression of receptors on normal cells, prompted research into the use of HAFP as a carrier/transporter of anticancer drugs (Severin, S. E. et al., Biochem. Mol. Biol. Int. 37(2):385-92, 1995; Severin, S. E. et al., Dokl. Akad. Nauk 366(4): 561-4, 1999) to target cancer cells specifically. It has been demonstrated that HAFP can target anticancer drug conjugates to tumor cells (Moskaleva et al., Cell Biol Int. 21(12):793-799, 1997; Sotnichenko et al., FEBS Letters 450: 49-51, 1999; U.S. Pat. No. 6,630,445 to Murgita). The high specificity of HAFP for cancer cells that bear receptors for AFP provides enhanced efficacy of drugs due to specific targeting to tumour cells. In addition, such modes of active agent delivery are safer for the patient as normal surrounding cells are spared.

HAFP bound with numerous anticancer drugs including doxorubicin, daunomycin, calichemicin, carboxyphosphamide, bleomycetin, chlorbutin, cis-platinum, methotrexate and caminomycin has been reported (Moskaleva et al., Cell Biol. Int. 21(12):793-799, 1997; Lutsenko et al., Tumor Biology 21(6):367-374, 2000). In these instances, the active agents were bound to HAFP using chemical conjugation methods, resulting in the covalent binding of HAFP to the anticancer agent. The optimal molar ratio of AFP:drug for AFP-drug conjugates that enables both binding of ingredients without loss of their biological activity and targeted delivery of the drug was found to be 1:2 (Feldman, N. B. et al., Biochemistry 65:1140-1145, 2000). The same molar ratio 1:2 can be achieved in noncovalent binding of AFP and Dioxin (Sotnichenko et al., FEBS Letters 450:49-51, 1999).

Herve et al. (in "Biological activities of alpha-fetoprotein", Florida Congresses, ed. Mizejewski, G. J., CRC Press, Inc., Boca Raton, Vol. 1, 1987) demonstrated warfarin and phenylbutazone binding sites on rat AFP, similar to those found on albumin. In addition, they demonstrated that these agents bind to AFP at the same large hydrophobic pocket as estrogens, fatty acids, pyrrazolic compounds and proprionic drugs. As reviewed in Mizejewski (Mizejewski, G. J., in "AFP and congenital disorders", ed. G. J. Mizejewski, Academic Press, Inc., 1985), whereas fatty acids are capable of binding to human AFP and to rodent AFP, phytoestrogens have been shown to be capable of binding to rodent AFP only suggesting inter-species differences in AFP binding capabilities.

The predominant source of AFP used in AFP/drug targeted delivery experiments has been human AFP extracted from either female retroplacental serum (Moskaleva et al., Cell Biol Int. 21(12):793-799, 1997) or human fetal material (www.alfetin.ru). Human fetal material is difficult to obtain due to limited sources (extracted from abortion material of up to 12 weeks gestation) and it is additionally expensive. In Russia, human fetal AFP is registered as an immune modulating injectable drug under the name "Alfetinum" (1 ampoule containing 0.075 mg of 95% pure AFP). Thus, alternative sources of AFP useful in the delivery of cytotoxic agents to cancer cells would be beneficial.

Anticancer agents with different modes of action have been reported to trigger apoptosis in chemosensitive cells (Fisher, Cell 78:539-542, 1994). Changes in mitochondrial function such as mitochondrial membrane permeability and/or permeability transition pore complex alterations play a major role in apoptotic cell death including cell death induced by anticancer agents (Kroemer et al., Immunol Today 18:44-51, 1997; Susin et al., J. Exp. Med. 186:5-37, 1997; Marchetti et al., J. Exp Med. 184:1155-1160, 1996; Zamzani et al., J. Exp. Med. 183:1533-1544, 1996; Decaudin et al., Can Res 57:62-67, 1997). Many conventional chemotherapeutic agents elicit mitochondrial permeabilization in an indirect fashion by induction of endogenous effectors, such as p53, that are involved in the physiologic control of apoptosis. However, the frequent mutation of p53 in many different human cancers renders the cancer refractory to conventional chemotherapeutic agents. The discovery of cytotoxic agents that act directly on the mitochondria such as lonidamine, arsenite, betulinic acid and CD437 has provided an alternative therapeutic strategy in circumstances where conventional drugs fail due to disruption of endogenous apoptosis induction pathways, such as those involving p53 (reviewed in Costantini et al., J. Natl. Cancer Institute 92:1042-1053, 2000). Cytotoxic agents that target mitochondria and induce cell apoptosis such as betulinic acid have been described (Fulda, S. et al., J. Biol. Chem. 18; 273 (51): 33942-8, 1998; Pezzuto et al. U.S. Patent Application Publication No. 20030186945). Costantini et al. reviews the mechanism of inducing apoptosis through mitochondrial destruction by alteration of mitochondrial membrane permeability and/or changes in the permeability transition pore complex (PTPC) and lists cytotoxic agents that target mitochondria to induce apoptosis (J. Natl. Cancer Inst. 92(13):1042-53, 2000).

The use of a single HAFP/anticancer agent conjugate (i.e. HAFP-estrone-doxorubicin conjugate) is considered to be a limiting factor in the treatment of malignant neoplasms due to the fact that many different types of cancer are refractory to chemotherapy and are said to exhibit multi-drug resistance (MDR) (Lehnert M., Eur. J. Cancer, 32A:912-920, 1996; Germann U. A., Eur. J. Cancer, 32A:927-944, 1996). Moreover, a number of anticancer agents are alkylating agents and antibiotics which induce tumour cell death by targeting DNA and thus, largely rely on an intact p53 signaling pathway (Bykov, V. J. et al., Nat. Med. 8(3):282-8, 2002). Given the large number of tumours that lack functional p53, these treatments are often ineffective.

There is therefore a need for improved mechanisms of delivering cytotoxic agents to cancer cells that are easily derived, inexpensive to produce, deliverable by non-invasive means and both efficient and specific in killing cancer cells.

The present invention may provide one or more of the foregoing advantages or other advantages which will become apparent to persons skilled in the art after review of the present application.

SUMMARY OF INVENTION

Briefly stated, the invention provides novel compositions comprising AFP and methods for preventing, treating or inhibiting a malignant neoplasm expressing an alpha-fetoprotein receptor (AFPR). The invention also provides for a process for butanol extraction of porcine alpha-fetoprotein obtained from blood and amniotic fluid extracted during early embryogenesis.

In one embodiment, the invention provides a composition comprising a non-covalent complex of an exogenous alpha-fetoprotein (AFP), and at least one apoptosis-inducing agent selected from the group comprising mitochondrial membrane permeabilizing agents, mitochondrial pore opening inducing agents, ionophores, caspase 9 activators, caspase 3 activators and retinoids, wherein the at least one apoptosis-inducing agent reversibly binds to the exogenous AFP. In one embodiment, the composition comprises two apoptosis-inducing agents capable of reversibly binding to the exogenous AFP. In another embodiment, the composition comprises apoptosis-inducing agents selected from the group comprising: atractyloside, betulinic acid, thapsigargin, rotenone, piericidin A, lonidamine, CD437, arsenic trioxide, A23187, Jonomicin, Vitamins D2 and D3, dexamethasone and Accutane.

The present invention also provides for the use of an exogenous AFP for delivery in a mammal of at least one apoptosis-inducing agent selected from the group comprising mitochondrial membrane permeabilizing agents, mitochondrial pore opening inducing agents, ionophores, caspase 9 activators, caspase 3 activators, and retinoids to a cancer cell, wherein the at least one apoptosis-inducing agent reversibly binds to the exogenous AFP, the cancer having at least one AFP receptor, and the exogenous AFP specifically binds to the at least one AFP receptor.

In one embodiment, the invention provides for the use of a composition comprising a non-covalent complex of: an exogenous alpha-fetoprotein (AFP); and at least one apoptosis-inducing agent selected from the group comprising mitochondrial membrane permeabilizing agents, mitochondrial pore opening inducing agents, ionophores, caspase 9 activators, caspase 3 activators and retinoids, in the preparation of a medicament for targeted delivery in a mammal of the at least one apoptosis-inducing agent to a cancer cell having at least one AFP receptor on a cell surface, wherein the at least one apoptosis-inducing agent reversibly binds to the exogenous AFP, and the exogenous AFP specifically binds to the at least one AFP receptor.

In another embodiment, the invention provides for the use of a composition comprising a non-covalent complex of: an exogenous alpha-fetoprotein (AFP); and at least one apoptosis-inducing agent selected from the group comprising mitochondrial membrane permeabilizing agents, mitochondrial pore opening inducing agents, ionophores, caspase 9 activators, caspase 3 activators and retinoids, for inhibition of proliferation of a cancer cell in a mammal, said cancer cell having at least one AFP receptor on a cell surface, wherein the at least one apoptosis-inducing agent reversibly binds to the exogenous AFP, and the exogenous AFP specifically binds to the at least one AFP receptor on the cell surface.

In yet another embodiment, the invention provides for the use of a composition comprising a non-covalent complex of: an exogenous alpha-fetoprotein (AFP); and at least one apoptosis-inducing agent selected from the group comprising mitochondrial membrane permeabilizing agents, mitochondrial pore opening inducing agents, ionophores, caspase 9 activators, caspase 3 activators and retinoids, for treating multidrug resistance in refractory malignant neoplasms, said refractory malignant neoplasms being comprised of cancer cells having at least one AFP receptor on a cell surface, wherein the at least one apoptosis-inducing agent reversibly binds to the exogenous AFP, and the exogenous AFP specifically binds to the at least one AFP receptor on the cell surface.

In another embodiment, the invention also provides a method of inhibiting cancer cell proliferation in a mammal, said cancer cell having at least one AFP receptor on a cell surface, wherein said method comprises administering to a mammal a therapeutically effective amount of a composition comprising a non-covalent complex of: an exogenous AFP; and at least one apoptosis-inducing agent selected from the group comprising mitochondrial membrane permeabilizing agents, mitochondrial pore opening inducing agents, ionophores, caspase 9 activators, caspase 3 activators and retinoids, wherein the at least one apoptosis-inducing agent reversibly binds to the exogenous AFP, and the exogenous AFP specifically binds to the at least one AFP receptor on the cell surface.

In another embodiment, the invention provides a method to treat multidrug resistance in refractory malignant neoplasms, said refractory malignant neoplasms comprising cancer cells having at least one AFP receptor on a cell surface, comprising administering to a mammal a therapeutically effective amount of a composition comprising a non-covalent complex of: an exogenous AFP; and at least one apoptosis-inducing agent selected from the group consisting of mitochondrial membrane permeabilizing agents, mitochondrial pore opening inducing agents, ionophores, caspase 9 activators, caspase 3 activators and retinoids, wherein the at least one apoptosis-inducing agent reversibly binds to the exogenous AFP, and the exogenous AFP specifically binds to the at least one AFP receptor on the cell surface.

In yet another embodiment, the invention provides a process for the extraction of porcine AFP from raw material using butanol comprising the sequential steps of:
(a) collecting blood and amniotic fluid from porcine embryos of from about 3 to about 14 weeks gestation;
(b) separating the blood and the amniotic fluid collected in (a) into a supernatant and a precipitate;
(c) collecting the supernatant resulting from (b);
(d) concentrating the supernatant resulting from (c) to form a concentrated solution;
(e) adding butanol to the concentrated solution of (d) to a final concentration of from about 5% to about 10% butanol in solution;
(f) stirring the butanol solution resulting from (e);
(g) separating the butanol solution resulting from (f) into an upper non-aqueous phase and a lower aqueous phase; and
(h) collecting the non-aqueous phase resulting from (g) to produce a final solution containing unbound porcine AFP.

Within certain specific embodiments, the compositions as described above are comprised of first and second apoptosis-inducing agents having unique dosages.

In one embodiment, the exogenous AFP used in the compositions is derived from a mammalian source. In another embodiment, the AFP is from a porcine source (PAFP). In other embodiments, the AFP is from a primate, bovine, equine, canine, feline or sheep source. The AFP may be isolated from nature or it may be a recombinant form of AFP.

DETAILED DESCRIPTION OF THE INVENTION

Figure 1:
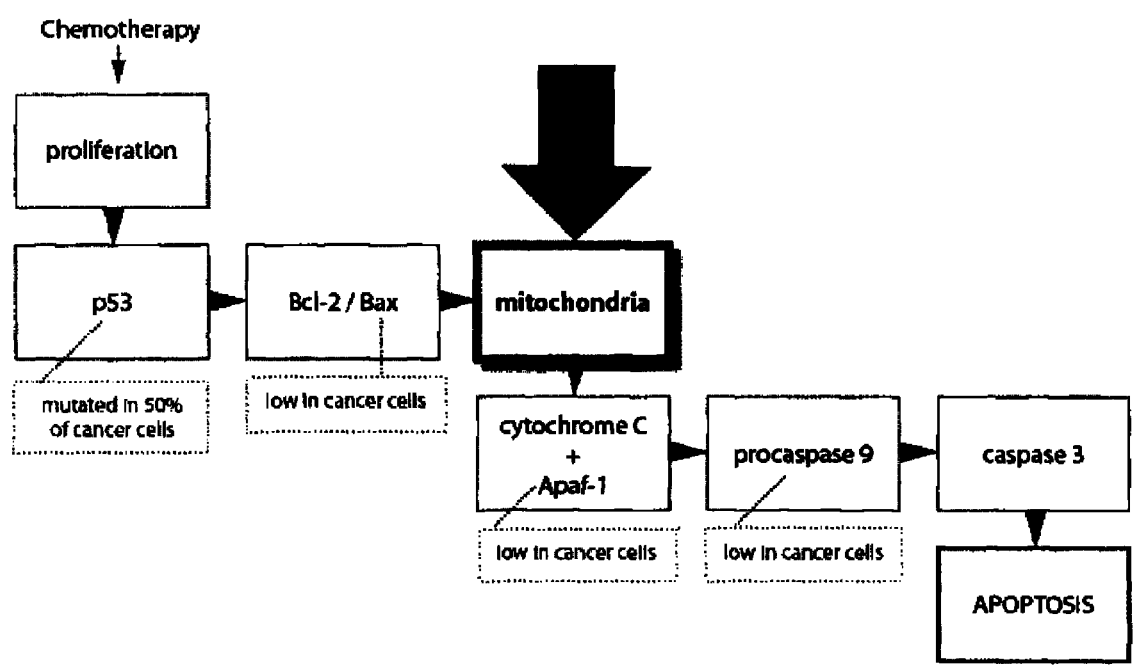
FIG. 1. Schematic of caspase-mediated apoptosis pathway in cancer cells subjected to chemotherapeutic agents.

The invention concerns compositions useful in targeted delivery of apoptosis-inducing agents to cancer cells. The compositions of the present inventions are comprised of exogenous AFP non-covalently complexed with compounds that induce apoptosis by directly affecting mitochondrial function, circumventing the need to elicit the apoptotic response through initial nuclear signaling. The source of AFP is porcine in one embodiment and porcine AFP extracted from embryos and amniotic fluid between 3 and 14 weeks gestation in another embodiment. Specific compounds useful in the present invention for non-covalent association with AFP include atractyloside, betulinic acid, thapsigargin, CD437, rotenone, piercidin A and lonidamine.

The term apoptosis-inducing agent as used herein refers to chemical or natural compounds with the ability to induce apoptotic cell death. In one embodiment of the invention, the apoptosis-inducing agent acts directly on mitochondria. Such compounds may elicit apoptosis by having effects on any of mitochondrial membrane permeability, induction of mitochondrial pore opening, on mitochondrial membrane potential as well as on activation of executive caspases, such as caspases 3 and 9.

In the context of the present invention, the apoptosis-inducing agent induces apoptosis of targeted cancer cells that express AFP receptors on the cell surface. Examples of apoptosis-inducing agents suitable for use with the current invention include or are derived from, but are not limited to, mitochondrial membrane permeability inducing agents such as atractyloside, betulinic acid, thapsigargin, CD437, lonidamine, arsenic trioxide and rotenone; caspase activators such as Pac-1 (Putt et al., Nature Chem. Biol. 2:543-550, 2006), ionophores such as calcimycin/A23187 and valinomycin; and retinoids such as Accutane and cis-retinoic acid; as well as well known chemotherapeutic agents such as dexamethasone; antibiotics such as oligomicin B; hydroxychloroquine phosphate; anti-oxidants such as quercetin, vitamin A, vitamin D2 and D3, curcumin, and capsaicin; and heavy metals such as zinc, lead, copper, nickel, and cadmium. See the world wide web at sigmaaldrich.com/catalog/search/TablePage/9560323; biomol.com/Online_Catalog/Online_Catalog/Products/36/?category- ld=234; emdbiosciences.com/html/cbc/apoptosis_inducers.html; and axxora.com/apoptosis_inducers_inhibitors/opfa.1014.2.1.0.html).

The term reversible as used herein means capable of being returned to the original ('unbound') condition, wherein the exogenous AFP, after delivering a first apoptosis-inducing agent (i.e. atractyloside, thapsigargin, betulinic acid, CD 437, arsenic trioxide, rotenone and lonidamine) to a tumor cell is recycled back to the extracellular medium in an unbound form where it is capable of binding to another compound for which it has inherent binding affinity (i.e. atractyloside, thapsigargin, betulinic acid, CD 437, arsenic trioxide, rotenone and lonidamine). It is possible that the exogenous AFP is recycled to the extracellular medium more than once. Previously, a number of in vitro studies demonstrated that AFP is capable of delivering polyunsaturated fatty acids (PUFAs) to cells via AFP receptor-mediated endocytosis and is later recycled undegraded to the extracellular medium (Torres et al., Int. J. Cancer 47:110-117, 1991; Uriel et al., in "Biological activities of alpha-fetoprotein", Florida Congresses, edited by Mizejewski, G J, CRC Press Inc., Boca Raton, Vol. 2, 1987; and Laborda et al., Int. J. Cancer 40:314-318, 1987). These studies suggest that recycled AFP is capable of binding to an apoptosis-inducing agent a second time upon return to the extracellular space.

The term a therapeutically effective amount as used herein means an amount of a composition of the present invention that, when administered to a patient, ameliorates or alleviates a symptom of the cancer (solid or non-solid) herein described. The specific dose of a composition administered according to this invention will, of course, be determined by the particular circumstances surrounding the case including, for example, the composition administered, the route of administration, the state of being of the patient, and the type of cancer being treated. Cancers suitable for treatment with the current invention are those cancers in which the cancerous cells express AFPRs. Examples of cancers with demonstrated expression of AFPR include, but are not limited to, bladder cancer, breast cancer, colon and rectal cancer, endometrial cancer, kidney cancer (renal cell), leukemia, liver cancer, lung cancer, melanoma, non-Hodgkin's lymphoma, ovarian cancer, pancreatic cancer, prostate cancer, skin cancer (non-melanoma), testicular cancer and thyroid cancer (Moro-Vidal, R., Curex Technologies Inc., www.biocurex.com).

The term patient means all mammals including humans. Examples of patients include humans, other primates, cows, dogs, cats, goats, sheep, pigs, horses and rabbits.

The present invention involves the use of exogenous alpha-fetoprotein (AFP) acting as a carrier or transporter of apoptosis-inducing agents directly to cancer cells resulting in the apoptosis of the cancer cells. U.S. Pat. Nos. 6,630,445 and 6,534,479 describe the use of recombinant human AFP for conjugation with cytotoxic agents. Previously, Nishi et al. (Ann. New York Acad. Sci. 259:109-118, 1975) demonstrated cross-species similarities amongst mammalian AFPs with respect to immunological and antigenic properties raising the possibility of alternative mammalian sources of AFP. Similarities between porcine and human AFP suggest that porcine AFP can be used to deliver apoptosis-inducing agents to cancer cells instead of human AFP (Table 1).

TABLE 1

Comparison of Human AFP (HAFP), recombinant Human AFP (rHAFP) and Porcine AFP (PAFP) properties.

| Property | HAFP | rHAFP | PAFP |
|---|---|---|---|
| % amino acid Similarity to Albumin | 40 | 40 | 38 |
| % Glycosylation | 3-4 | 0 | 3-4 |
| Glycosylation sugars | Different | 0 | unknown |
| Microheterogeneity | Yes | No | No |
| Possibility of pathogenic contamination from source | Yes | No | No |
| Ethical issues around source | Yes | No | No |
| Fatty acid binding ability | Yes | unknown | Yes |
| Hydrophobic ligand affinity | Yes | unknown | Yes |
| Anticancer activity (AFP-mediated delivery of apoptosis-inducing agent bound to cancer cells) | Yes | unknown | Yes |

(NCBI Blast analysis is available on the world wide web at ncbi.nlm.nih.gov/blast/; Parker, M. H. et al., Protein Expression and Purification, 38:177-183, 2004).

The term exogenous as used herein means originating from outside the patient or organism.

The invention relates to a composition of exogenous AFP and a first apoptosis-inducing agent reversibly bound to exogenous AFP in vitro to form an AFP-first apoptosis-inducing agent complex, and can also include a second apoptosis-inducing agent wherein the first apoptosis-inducing agent and the second apoptosis-inducing agent are anticancer drugs (i.e. atractyloside, thapsigargin, betulinic acid, CD 437, arsenic trioxide and lonidamine) and wherein the second apoptosis-inducing agent is capable of reversibly binding to recycled, exogenous AFP in vivo. The first apoptosis-inducing agent and the second apoptosis-inducing agent may be the same (i.e. betulinic acid) or they may be different (i.e. betulinic acid and CD 437).

The presence of multiple binding domains on AFP raises the possibility that more than one class of apoptosis-inducing agent is capable of binding to AFP simultaneously in vitro (Hirano, K. et al., Biochem. J., 231:189-191, 1985; Mizejewski, G. J., Exp. Biol. Med. 226(5): 377-408, 2001). This is due to the fact that some binding domains interact with hydrophobic drugs, while other binding domains interact with hydrophilic or amphiphilic drugs.

According to one embodiment of the invention, a cancer patient will receive a daily dosage of the inventive composition wherein the total daily intake of AFP will be between 0.07 mg and 1.2 mg depending on the patient and the aggressiveness of the disease. This concentration of AFP is based on the physiological concentrations of AFP commonly found in circulation during pregnancy. In murine counterparts, comparable dosages are between 0.0014 mg and 0.024 mg according to guidelines provided in "Natural Compounds in Cancer Therapy", (Boik, J., *Natural Compounds in Cancer Therapy*. Oregon Medical Press, 2001, pp. 8-10).

The composition of the current invention may contain varying molar ratios of the first and second apoptosis-inducing agent, such as from an equimolar ratio to an overabundance of the first apoptosis-inducing agent in relation to AFP and from an equimolar ratio to an overabundance of the second apoptosis-inducing agent in relation to AFP. The in vitro binding conditions of the first apoptosis-inducing agent and AFP will depend on the properties of the first apoptosis-inducing agent (i.e. hydrophilic or hydrophobic). Typically, AFP is mixed with the first apoptosis-inducing agent where the molar ratio of the AFP and the first apoptosis-inducing agent ranges from 1:1 to 1:3. More typically, AFP is mixed with the first apoptosis-inducing agent where the molar ratio of the AFP and the first apoptosis-inducing agent ranges from 1:1 to less than 1:3 The first apoptosis-inducing agent may be composed of one or more anticancer drugs. However, if multiple drugs are to be used, it must be ascertained that each binds to a different binding domain on AFP as mentioned above.

The extracted material is subjected to diafiltration to eliminate small, unbound molecules without disturbing the PAFP–apoptosis-inducing agent complex. Previously, Sotnichenko et al. (FEBS Letters 450:49-51, 1999) demonstrated that human fetal AFP forms a complex with dioxin at a 1:2 molar ratio and that gel filtration effectively eliminates unbound molecules without disturbing the AFP-dioxin complex.

Typically, the second apoptosis-inducing agent is present in an amount that is at least 10-fold lower than the amount used in the methods described in the prior art. For example, Pezzuto et al. (U.S. Patent Application Publication No. 20030186945) recommend a dosage of betulinic acid of 3000 µg (daily oral dosage from 0.2 mg to 500 mg) whereas in the current invention, the dosage of betulinic acid (second apoptosis-inducing agent) can be as low as 150 µg. In the present invention, 0.6 mg of PAFP is complexed with 0.007 mg of betulinic acid. In another embodiment, 0.15 mg of unbound betulinic acid is included in the formulation.

PAFP is unstable and can aggregate, precipitate or become inactivated during manipulations such as those of the chemical conjugation process described previously (G. J. Mizejewski, "Alpha-fetoprotein", in Monographs on Endocrinology, ed. Ulrich Westphal, Steroid-protein interactions II, Springer-Verlag, Berlin, New-York, Tokyo, 1986, pp. 320-356; Nunez, E. A. et al, The physiochemical and biological properties of AFP depend on its ligand environment, J. Nucl. Med. Allied Sci., 33:18-16, 1989). The time required to achieve in vitro binding of PAFP to the first apoptosis-inducing agent at 18-25° C. in the present invention is 10 minutes, which is considerably shorter than the time required by noncovalent binding processes described in the prior art, where the standing time at 18-25° C. is 10-12 hours (see, for example, U.S. Pat. No. 6,878,688 to Pak et al.). The reduced time to achieve in vitro binding of PAFP and the first apoptosis-inducing agent may be attributed to: (1) a higher concentration of unbound PAFP available for binding present in the concentrate obtained by the ultrafiltration and butanol extraction methods of the present invention, and (2) the microhomogenicity of PAFP obtained by the current process compared to the HAFP obtained by other methods which, as stated above, is microheterogeneous (Wu, J. T. and Clayton, F., "Detection and isolation of various isoforms of human AFP", in "Biological activities of AFP", CRC Press, 1987, Boca Raton, Fla., vol. 2, pp. 3-14; Mizejewski, G. J., Exp. Biol. Med., vol. 226(5):377-408, 2001).

Typically, the first apoptosis-inducing agent is one class of anticancer drug and is present in a daily concentration of no more than 150 µg. Apoptosis-inducing agents useful in the present invention are preferably selected from the group comprising mitochondrial membrane permeabilizing agents, mitochondrial pore opening inducing agents, caspase 9 activators, caspase 3 activators, ionophores and retinoids.

Multidrug resistance (MDR) is frequently associated with high expression levels of the gp170 pump at the surface of cancer cells (Lehnert M., Eur J Cancer 32A: 912-920, 1996; Germann U. A., Eur. J. Cancer 32A:927-944, 1996; Thomas, H., et al., Cancer Control 10(2):159-165, 2003). However, MDR is also known to occur in cells with damaged p53 or upregulated expression of an apoptotic inhibitor such as Bcl-2 (Jaattela, M., Exp. Cell Res. 248:30-43, 1999). Many chemotherapeutic agents have targets upstream of p53 activity, such as DNA, RNA, telomerases and topoisomerases. These agents are ineffective in inducing apoptosis in cells with damaged p53 or upregulated Bcl-2 (Evan, G. I. and Vousden, K. H., Nature 411:342-348, 2001) (FIG. 1). Moskaleva et al. (Cell Biol. Int., 21(12):793-799, 1997) demonstrated that AFP-drug conjugates were effective at killing multidrug resistant cancer cells that overexpress MDR (p-glycoprotein drug efflux pump) suggesting that receptor-mediated endocytosis of AFP-drug conjugates overcomes multidrug resistant cancers. In the present invention, apoptosis-inducing agents are selected based on their ability to induce apoptosis at the level of the mitochondria, downstream of p53. Through their effects on mitochondrial membrane permeability and mitochondrial pore transition and/or caspase activation, these apoptotic inducers are capable of eliciting cytotoxic effects on multidrug resistant cancer cells (FIG. 1).

Preferably, the apoptosis-inducing agents for use in the present invention are derived from natural sources (Pessayre et al., "Apoptosis Trigged by Natural Substances", in "Apoptosis and Its Modulation by Drugs", eds. R. G. Cameron, G. Feuer, Springer Press, 2000, pp. 86-108). For example, betulinic acid is derived from betulin, a substance found in abundance in the outer bark of white birch trees (*Betula alba*). Typical apoptosis-inducing agents useful in the present invention include, but are not limited to, thapsigargin, atractyloside, betulinic acid, CD437, arsenic trioxide, rotenone, piercidin A and lonidamine.

Other examples of apoptosis-inducing agents suitable for use with the current invention include or are derived from, but are not limited to, dexamethasone, oligomicin B, hydroxychloroquine phosphate, quercetin, vitamin A, vitamin D2 and D3, curcumin, capsaicin, and heavy metals such as zinc, lead, copper, nickel, cadmium, and chemotherapeutic agents.

The compositions of the present invention may be delivered to a cancer cell by any currently known method of administration including but not limited to oral dosage forms (i.e. capsules, softgels, and tablets), suppositories, inhalations, nose or eye drops, bandages; smell powders, injectables, linaments and topical formulations. In one embodiment, the compositions are prepared for oral dosage as softgels. In another embodiment, the compositions are prepared for intravenous dosage as an injectable.

EXAMPLE 1

PAFP Isolation and Purification

PAFP was extracted from the liver and blood of porcine embryos, the amniotic fluid, and the placenta. The fetal stage at which the extraction is performed is crucial due to the fluctuating post-translational properties of PAFP that can affect both its biological activity (e.g. receptor binding) as well as its ability to bind to apoptosis-inducing agents. PAFP extracted from early gestation (earlier than 3 weeks) or later gestation (beyond 14 weeks) fetal material is differently glycosylated compared to PAFP extracted from fetal material of between 3 and 14 weeks gestation (Ruoslahti, E. et al., Int. J. Cancer, 22:515-520, 1978; Keel, B. A. et al., in "Biological Activities of Alpha1-Fetoprotein", Boca Raton, Fla., CRC Press vol 2, pp. 24-31, 1989; Mizejewski, G. J., Exp. Biol. Med. 226(5):377-408, 2001; Parker, M. H. et al., Protein Expression and Purification, 38:177-183, 2004; Mizejewski, G. J., in "Monographs on Endocrinology", ed. Ulrich Westphal, Steroid-protein interactions II, Springer-Verlag, Berlin, New-York, Tokyo, 1986, pp. 320-356). The different states of glycosylation have been shown to affect the binding properties of HAFP, thus, the timing of the extraction of the fluids from the embryo is critical as the glycosylation of PAFP varies during embryogenesis and the fluid yield diminishes significantly after the 14th week of gestation. Ideally, porcine fetal material was collected between the 3rd and 14th week of embryogenesis and subjected to the extraction process.

Following extraction, the blood and amniotic fluid (herein after the "raw material") were maintained at 4-10° C. for 12 to 24 hours in order to allow natural sedimentation to occur. The supernatant was collected and transferred to a different container and subsequently concentrated 3-5 times by ultrafiltration using a 50 kDa membrane. During the ultrafiltration process, the temperature did not exceed 15° C. This concentration step resulted in a high yield of PAFP. Butanol was then added to a final concentration of between 5%-10%; typically the final concentration of butanol was about 8%. The raw material and butanol were stirred for 2 minutes and the mixture allowed to incubate for an additional minute enabling separation of the solution into an upper non-aqueous phase and a lower aqueous phase. The upper non-aqueous layer containing unbound PAFP was retained and subjected to diafiltration in order to remove residual butanol from the mixture. The resulting solution containing PAFP was subjected to in vitro binding with apoptosis-inducing agents for use in treating refractory cancer.

The method of PAFP extraction of the present invention is advantageous over traditional methods of AFP extraction in that it results in increased and more highly concentrated yields of unbound PAFP. By unbound is meant PAFP not bound to endogenous binding partners. As a result of higher concentrations of unbound PAFP, it was anticipated that increased concentrations of PAFP bound to apoptosis-inducing agents of interest are achievable.

Figure 2:
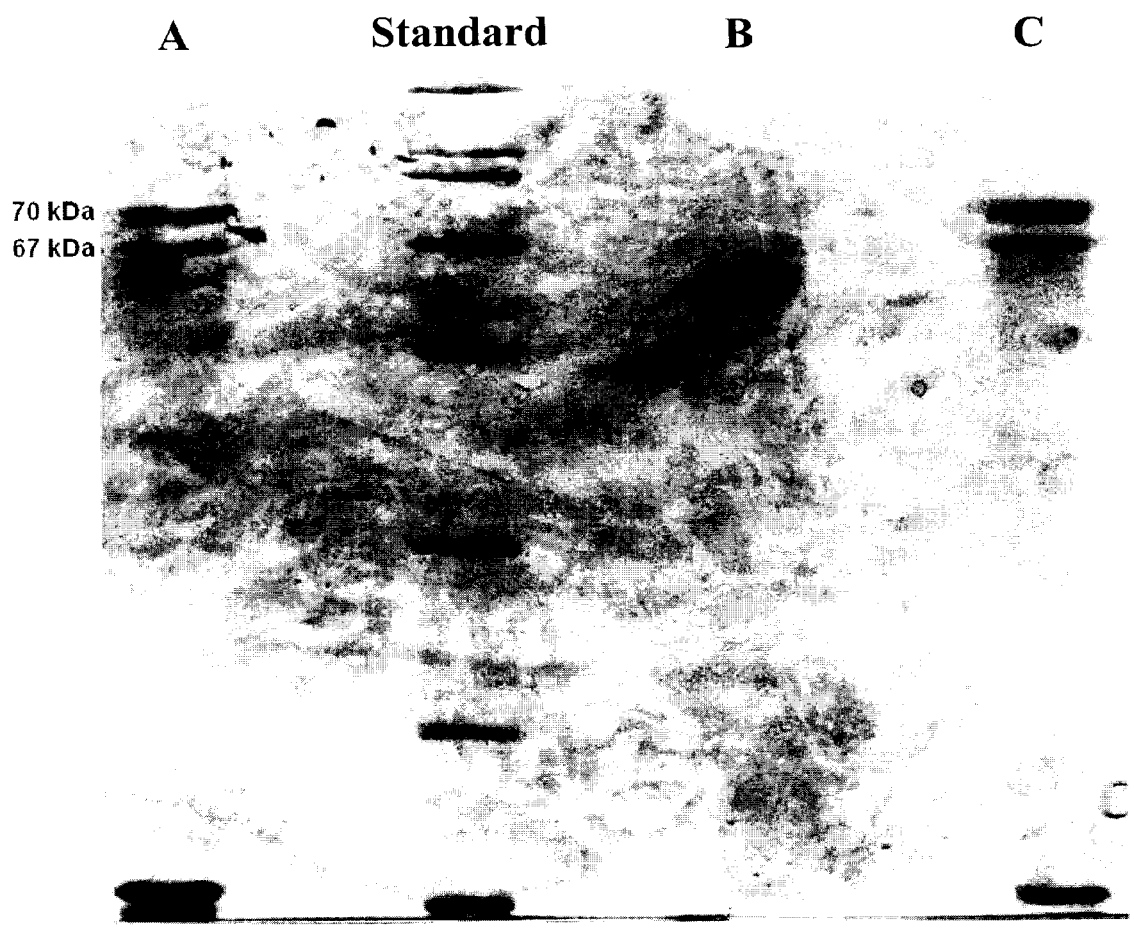
FIG. 2. Gel Electrophoresis of AFP concentrate alone (lane "C"), AFP concentrate bound to Atractyloside (lane "A") and standard molecular weight markers. Lane "B" is discarded for another experiment.

PAFP extracted by the methods detailed above was subjected to polyacrylamide gel electrophoresis (FIG. 2). Two major protein bands were evident upon Coomassic gel staining (FIG. 2, lanes A and lane C). The upper band (approximately 70 kDa) corresponds to PAFP and the lower band (approximately 67 kDa) corresponds to albumin.

EXAMPLE 2

PAFP has Similar Binding Properties Compared to HAFP

Previous studies had not addressed whether or not PAFP possesses similar biological properties compared to HAFP. PAFP extracted by the methods detailed above was analyzed using two different immune-enzyme kits in order to detect the presence of PAFP in the extraction obtained from the methods detailed above. PAFP samples were compared to AFP isolated from human serum and amniotic fluid. Initially, samples were subjected to the membrane EIA Alpha-fetoprotein test (catalog #410-1, IND Diagnostic Inc., Vancouver, Canada) which incorporates a monoclonal antibody to HAFP. PAFP did not produce a reaction with the EIA Alpha-fetoprotein test kit compared to the human AFP sample suggesting potential differences in the chemical structure of PAFP versus human AFP. A second test kit incorporating a polyclonal antibody to HAFP (catalog number T-8456, AFP-EIA-BEST-Strip, Vector-BEST, Novosibirsk, Russia) was then used to assay the presence of PAFP in the extraction. A positive reaction occurred indicative of the ability of PAFP to react with antibodies raised against human AFP. The results of the immunoassay studies suggest PAFP is capable of recognition by antibodies to HAFP, suggesting PAFP is structurally similar to HAFP.

It has been previously demonstrated that HAFP itself is capable of inducing apoptosis. Induction of tumor cell death was shown at high physiological doses of AFP (>250 mg/mL), but not at low doses (<200 mg/mL) (Dudich et al., Eur. J. Biochem. 266:1-13, 1999). In addition, studies have shown HAFP is capable of binding to various hydrophobic and hydrophilic compounds (Hirano, K., et al., Biochem. J. 231; 189-191, 1985). However, it was not known if PAFP could similarly induce apoptosis or other downstream biological responses and if PAFP is, similar to HAFP, capable of binding to various agents due to differences in amino acid sequence of PAFP compared to HAFP (82% amino acid similarity) (Kim et al., Animal Genetics, 33:468-485, 2002).

Studies conducted in a murine cancer model demonstrated the ability of PAFP to deliver apoptosis-inducing agents (e.g. atractyloside, thapsigargin and betulinic acid) to cancer cells and, consequently to reduce the tumour burden (see Examples 4 and 6). These results were consequently replicated in a human study where apoptosis-inducing agents bound to PAFP were found to elicit anti-tumour effects (see Example 5, 7 and 8). Together, the data suggest that PAFP is recognized by both human and murine AFP receptors.

EXAMPLE 3a

In Vitro Binding of PAFP and an Apoptosis-Inducing Agent

PAFP obtained from the extraction procedure detailed above was combined with an apoptosis-inducing agent. for one minute and allowed to incubate for an additional 10 minutes at 10-15° C. While longer incubation periods were acceptable, extension of the incubation time did not provide significant benefit with regards to amount of agent bound to PAFP. The PAFP– apoptosis-inducing agent mixture was then subjected to steps of ultrafiltration using a 50 kDa membrane and diafiltration in order to remove small molecules and other impurities, for example salts used as a biological buffer in previous extraction steps during the collection of raw material. The diafiltration step additionally assisted in eliminating unbound apoptosis-inducing agent remaining. The retentate contained the PAFP– apoptosis-inducing agent mixture useful in subsequent steps.

A final filtration step was performed using a 0.22 micron membrane in order to filter sterilize the resulting solution. Albumin remained in the mixture but does not interfere with the efficacy of the present inventive compositions.

The resulting solution was flash-frozen at −45° C. until it is completely frozen. The PAFP– apoptosis-inducing agent composition was then dried using a freeze dryer until the layer was completely dried. The freeze dried PAFP– apoptosis-inducing agent composition was then ground to fine particles ensuring that the temperature of the powder didn't exceed 35° C. A powder of 80 mesh or smaller was obtained in order to facilitate the incorporation of the composition into various preparations or delivery systems. The precise quantity of PAFP in the powder can be calculated using HPLC or PAAG-electrophoresis data.

EXAMPLE 3b

PAFP-Atractyloside

One liter of PAFP retentate having a final total protein concentration of 35 g/L, and approximately 21 g/L PAFP, was combined with 250 mg of atractyloside (MW=803) dissolved in 50 mL of water in order to achieve a 1:1 molar ratio PAFP:actractyloside. The solution was allowed to mix for 10 minutes at 4-15° C. and was then ultrafiltrated and diafiltrated with 2-3 volumes water. One liter of the final solution was subjected to freeze-drying to produce the PAFP-atractyloside composition.

EXAMPLE 3c

PAFP-Thapsigargin

Half a liter of PAFP retentate having a total protein concentration of 8 g/L and approximately 1.7 g/L PAFP, was combined with 10 mg of Thapsigargin (MW=650) dissolved in 10 mL of alcohol in order to achieve a 1:1 molar ratio PAFP:thapsigargin. The solution was allowed to mix for 30 minutes at 15-25° C. and was then ultrafiltrated and diafiltrated with 2-5 volumes water. Two hundred milliLiters of the final solution was subjected to freeze-drying to produce the PAFP-thapsigargin composition.

EXAMPLE 3d

PAFP-Betulinic Acid

Two liters of PAFP retentate with a total protein concentration of 20 g/L and approximately 14 g/L of PAFP was combined with 500 mg of betulinic acid (MW=456) dissolved in 100 mL of DMSO which was added dropwise in order to achieve a 1:1 molar ratio PAFP:betulinic acid. The solution was allowed to mix for 10 minutes at 25-37° C. and then subjected to diafiltration. One liter of the final solution was subjected to freeze-drying to produce the PAFP-betulinic acid composition.

EXAMPLE 4

In vivo murine leukemia model: PAFP+apoptosis-inducing agent kills tumor cells in the mice after 24 days of tumor cells inoculation.

Mice of the $DBA_2$ strain were inoculated subcutaneously in the side of the body with 20,000 P-388 murine leukemia cells, previously shown to express AFP receptors (Severin et al., Dokl. Acad. Nauk, 366(4):561-564, 1999; Moro-Vidal, R., Curex Technologies Inc., www.biocurex.com). All animals survived post-inoculation. Ten mice each were subjected to one of the following daily treatments:
1—preparation A (PAFP-atractyloside composition)
2—preparation T (PAFP-thapsigargin composition)
3—preparation S (spleen extract)
4—preparation A+S
5—preparation T+S
6—control oil
7—control water Each group consisting of 10 mice received daily 0.2 mL oral dosages of the indicated treatment in oil delivery vehicle beginning at day 2, the day after P-388 cell inoculation. The animals were evaluated for tumour growth on day 24 post-inoculation. The results are summarized in Table 2.

TABLE 2

| Treatment Group | Survival % (Day 24) | Average Tumor size(cm³) |
|---|---|---|
| 1- PAFP-atractyloside composition, 0.02 mg/day (preparation A) | 90% | 0.92 +/− 1.17 |
| 2- PAFP-thapsigargin composition, 0.08 mg/day (preparation T) | 80% | 1.33 +/− 0.68 |
| 3- spleen extract, 4.0 mg/day (preparation S) | 70% | 2.97 +/− 2.62 |
| 4- preparation A + S (0.02 mg A + 4.0 mg S) | 40% | 4.17 +/− 0.65 |
| 5- preparation T + S (0.08 mg T + 4.0 mg S) | 20% | 5.59 +/− 3.36 |
| 6- control oil | 10% | 6.34 |
| 7- control water | 0% | No living animals to measure |

Figure 3:
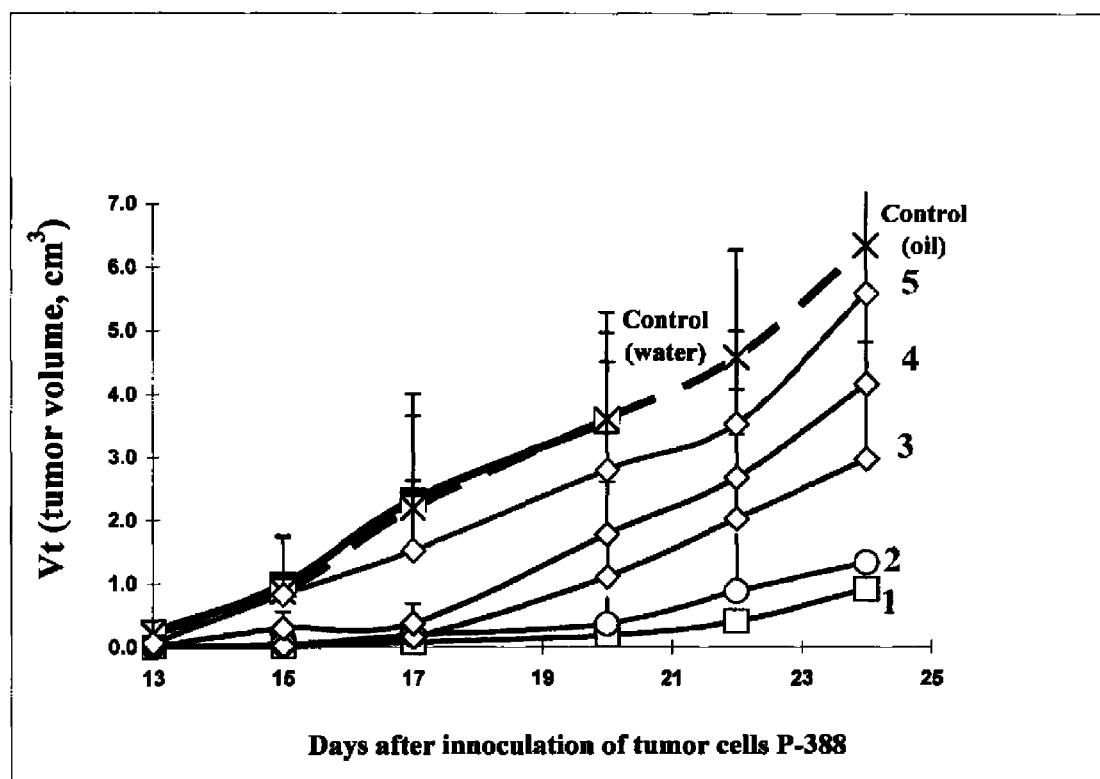
FIG. 3. Tumour volume measured in $cm^3$ as a function of time measured in days in a murine model of leukemia following treatment with PAFP-apoptosis-inducing agent compositions. P-388 leukemia cells were injected subcutaneously into $DBA_2$ mice. One day post-inoculation animals were treated daily with one of: 1. preparation A (PAFP-atractyloside (A)); 2. preparation T (PAFP-thapsigargin (T)); 3. preparation S (Spleen extract (S)); 4. preparation A+S; 5. preparation T+S; 6 control oil; or 7 control water.

The growth of P-388 lymphocytic leukemia cell line inoculated subcutaneously into the sides of mice and treated daily as indicated beginning one day post-inoculation is shown in FIG. 3.

Figure 4:
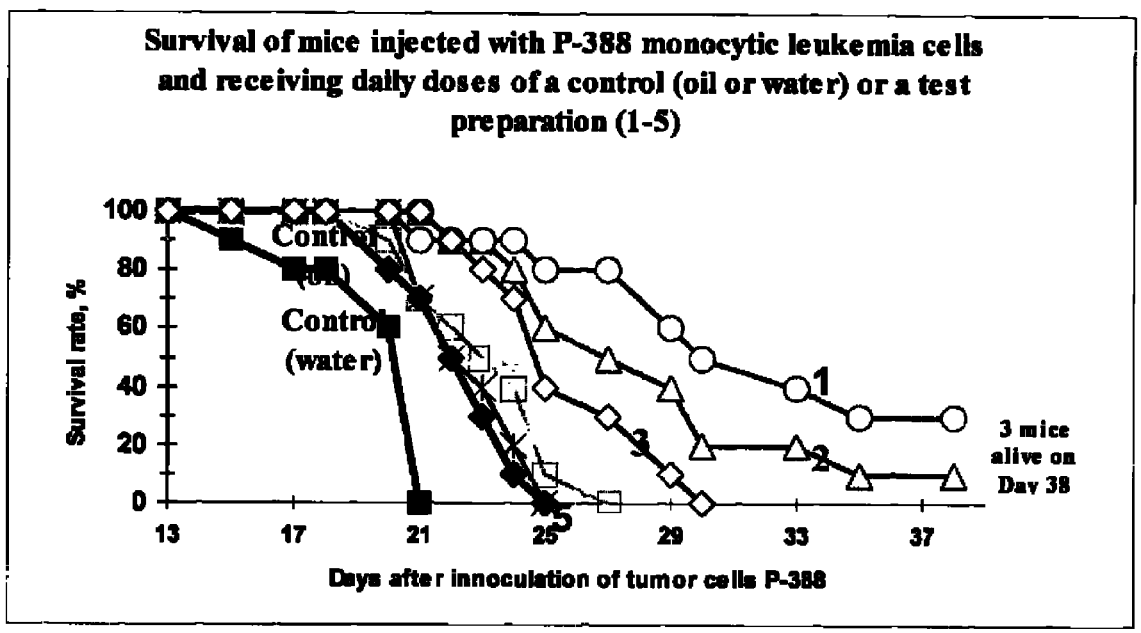
FIG. 4. Survival rate in $DBA_2$ mice following subcutaneous injection of P-388 leukemia cells and subsequent daily treatment one day post-inoculation with one of: 1. preparation A (PAFP-atractyloside product); 2. preparation T (PAFP-thapsigargin product); 3. preparation S (Spleen extract); 4. preparation A+S; 5. preparation T+S; 6 control oil; or 7 control water.

Results:
1. The growth of the tumors in group 1 (PAFP-atractyloside) and group 2 (PAFP-thapsigargin) animals was suppressed on average by 79% and 53% respectively compared to control groups 6 (oil) at day 24 post-inoculation. At day 22 post-inoculation, the growth of the tumors was suppressed on average by 85% and 79% respectively compared to control group 7 (water).
2. The survival rate was measured when 50% of the animals in each group of 10 (e.g. 5 animals) were alive. 50% survival rates in group 1 animals (day 30), which were administered the PAFP-atractyloside composition, increased 1.4 times compared to survival rates in animals that received water as a control (group 7) (day 21). 50% survival in group 2 animals (day 27), which were administered PAFP-thapsigargin composition, increased 1.28 times compared to control animals (FIG. 4).
3. 38 days post-inoculation, 3 of 10 mice receiving PAFP-atractyloside ("Preparation A") daily treatments were still alive and one of 10 mice being administered PAFP-thapsigargin ("Preparation T") was still alive (FIG. 4). All mice in the water control group were dead by day 24 while all mice in the oil control group were dead by day 25.
4. In one of three mice still alive 38 days post-inoculation receiving daily treatments of "Preparation A", tumour regression was observed (Table 3).

TABLE 3

| | Days Post-Inoculation | | | | | | |
|---|---|---|---|---|---|---|---|
| | 13 | 15 | 17 | 20 | 22 | 24 | 38 |
| Tumour Size (cm³) | 0 | 0.05 | 0.05 | 0.05 | 0.03 | 0.01 | *ND |

*ND = not determined

Similar tumor growth regression was demonstrated by Severin et al. using AFP as a delivery vehicle for the antibiotic esperamicin A1 to which it was covalently conjugated (Severin, S. E. et al., Dokl. Akad. Nauk. 366(4): 561-4, 1999).

Conclusions:
1. "Preparation A" and "Preparation T" comprised of PAFP-atractyloside and PAFP-thapsigargin respectively, at the demonstrated concentrations, inhibited tumour growth.
2. Administration of apoptosis-inducing agents atractyloside and thapsigargin bound to PAFP extended survival in a murine model of leukemia.

EXAMPLE 5

In Vivo Data Tumor: PAFP-atractyloside Composition Kills Tumor Cells in Humans

Eight patients classified as stage IV in their cancer progression by their respective doctors were administered oral dosages of PAFP-atractyloside composition in capsule form (2-6 capsules) daily for one month. The progress of these patients was then followed by their respective doctor for an additional four months. The patients themselves reported enhanced quality of life. According to CT scans performed on these patients, those receiving the PAFP-atractyloside treatment experienced a reduction in the growth rate of the primary tumor, a reduction in the size of the primary tumor in some cases, as well as a reduction in extent of metastasis. The conclusions of the initial human study are as follows:

1. The oral intake of PAFP-atractyloside product (in starch and oil delivery vehicle) in daily doses of 2-6 capsules was found to be safe and associated with minimal side effects during the course of the treatment.
2. The decrease in primary and metastatic tumour size as well as pain at the metastatic site confirmed the specific anti-cancer action of PAFP-atractyloside product.
3. Marked improvements in quality of life measured by patient-described enhancement of physical activity and general well being were observed in patients that received the PAFP-atractyloside composition administration either alone or in combination with other drugs.
4. The data indicated a dose-dependent response in patients who were administered the PAFP-atractyloside composition as determined by the observed reduction in both primary and metastatic tumor masses.
5. Administration of PAFP-atractyloside was only rarely accompanied by an acute immune reaction (increase in body temperature, local pain at the site of tumor/mestastasis) as the dose was increased.
6. The reduction in tumour burden in stage 1V cancer patients in response to administration of the PAFP-atractyloside composition suggested the composition is orally bioavailable.

EXAMPLE 6

Figure 5:
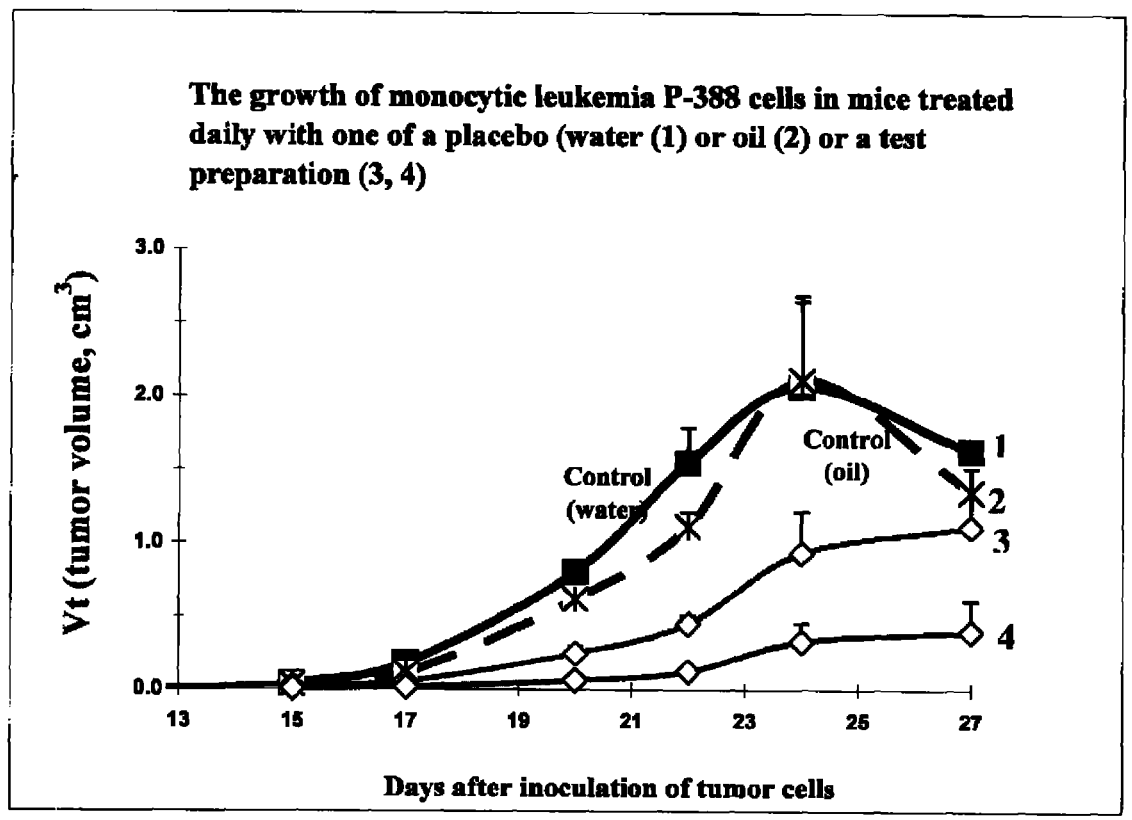
FIG. 5. Tumour volume measured in $cm^3$ as a function of time measured in days following subcutaneous injection of P-388 leukemia cells into $DBA_2$ mice and subsequent daily treatment beginning one day post-inoculation with one of: 1. control (water); 2. control (oil); 3. PAFP-betulinic acid; 4. PAFP-betulinic acid plus additional unbound betulinic acid.

In Vivo Data—Leukemia: a composition comprising exogenous PAFP reversibly bound to a first apoptosis-inducing agent in vitro and a second apoptosis-inducing agent kills tumor cells in mice
Daily treatments consisted of:
1—Control water
2—Control oil
3—PAFP bound to a first apoptosis-inducing agent (betulinic acid) in vitro (PAFP-betulinic acid composition)
4—PAFP bound to a first apoptosis-inducing agent (betulinic acid) in vitro (PAFP-betulinic acid composition) in combination with additional, unbound betulinic acid Mice were inoculated with 20,000 P-388 murine leukemia cells on day 1 and on day 2 were administered daily oral dosages of 0.2 mL water (1) or oil (2) control treatments or 0.2 mL dosages of test preparations 3 or 4. Experiments were designed to include 10 mice in each treatment group. FIG. 5 shows a graph of the growth of P-388 leukemia cells as a function of time in animals receiving one of a daily oral dosage of water (1), oil (2), PAFP-bound betulinic acid (3) or PAFP-bound betulinic acid combined with additional, unbound betulinic acid (4) where each of the latter two preparations are suspended in 0.2 mL of oil.

Group 4 treatments were prepared by dissolving excess betulinic acid in DMSO as 0.5 mg/mL then adding 2 µL (1 µg) of this solution to the 0.2 mL of PAFP-bound betulinic acid preparation. Once the PAFP-bound betulinic acid is delivered to a tumour cell, PAFP is hypothesized to be recycled extracellularly enabling the exogenous PAFP to bind to the excess betulinic acid in the tumour microenvironment for subsequent delivery to tumour cells based on the results of in vitro studies which demonstrated that $I^{125}$-labeled AFP is endocytosed by neoplastic lymphoid cell lines and released practically undegraded from the cells (Torres et al., Int. J. Cancer 47(1):110-117, 1991).

Betulinic acid (BA) has been used to treat malignant melanoma (U.S. Patent Application Publication No. 2003/0186945), however, large doses of BA are required (0.2 mg-500 mg daily). PAFP is mixed with BA in a molar ratio of 1:2 where the composition is present in the amount for human of 0.6 mg within 0.2 mL of oil acting as the carrier. In a weight ratio, betulinic acid is present at a daily dose of 0.008 mg. When in complex with PAFP, betulinic acid has been found to be effective in humans at microgram concentrations. Boik (Natural Compounds in Cancer Therapy, 2001) provides the following equation to calculate equivalent murine oral dose from human dose: human dose (grams/kg)=mouse dose (mg/kg)/104. A human weight of 75 kg and a mouse weight of 0.02 kg gives: 0.0006 g (human dose)×104=mouse dose (mg/kg) =0.0624 mg/kg. For a 0.02 kg mouse, the dose can be calculated as 0.0624 mg/kg×0.02 kg=0.01248 mg or 12 µg. The coefficient for calculating murine dose from human dose is 600 µg (human daily dose)/12 µg (mouse daily dose)=50. In cases where an excess second apoptosis inducer is included in the dose, this second apoptosis inducer is added later in a oil suspension form to an already prepared oil suspension of the first complex (PAFP/first apoptosis inducer). For example, a typical murine dose consists of 7 µg of PAFP-Betulinic acid complex in dry form admixed with 0.05 mL of oil and combined with 0.15 mg of Betulinic acid dissolved in oil to final volume of 0.2 mL of oil.

Comparison of tumour volume in animals receiving PAFP-bound betulinic acid (group 3) in the absence of excess betulinic acid to tumour volume in animals receiving PAFP-bound betulinic acid in combination with excess betulinic acid (group 4) indicates the latter treatment resulted in reduced tumour volume. The results suggest added therapeutic benefit in the combination of PAFP-bound betulinic acid with excess unbound betulinic acid. The data further suggest that apoptosis-inducing agents capable of binding to PAFP can be used to treat malignant neoplasms, the cells of which express AFP receptors, by: 1) delivery of the PAFP-bound with apoptosis-inducing agent to the tumor cell and 2) consequent delivery of an additional, second apoptosis-inducing agent capable of binding to PAFP in vivo to improve the therapeutic outcome.

The results demonstrate that inclusion of excess, unbound betulinic acid in the PAFP-bound betulinic acid preparation is more effective at reducing tumour growth than PAFP-bound betulinic acid alone. Furthermore, the data suggest a therapeutic advantage in using a second apoptosis-inducing agent in the inventive composition.

EXAMPLE 7

In Vivo Data—Tumor: a composition comprising exogenous PAFP reversibly bound to a first compound in vitro and a second compound used to kill solid tumour type of cancers in human patients.

Preliminary results in 5 patients (4 women and one man) with solid tumours with or without metastases:
Patient #1: woman, 57 years old, localized breast cancer
Patient #2: woman, 63 years old, breast cancer metastasized to the bones
Patient #3: woman, 44 years old, with ovarian breast cancer.
Patient #4: woman, 60 years old, breast cancer with metastasis to the lymph nodes
Patient #5: man, 58 years old, testicular cancer.

The aim of the study was to evaluate response to PAFP-betulinic acid compositions in patients with solid type cancers classified as inoperable, refractory to existing treatments or recurrent post-operation.

The patients took a daily dosage of two softgels on an empty stomach, one in the morning and one before bedtime. Each softgel was comprised of PAFP-betulinic acid product (i.e. betulinic acid reversibly bound to exogenous PAFP in vitro) and excess betulinic acid (i.e. additional betulinic acid not bound to PAFP). The PAFP-betulinic acid product was provided in a single unit dosage of 300 μg of PAFP and 6 μg of betulinic acid per softgel. The excess or additional betulinic acid was present as 150 μg per softgel.

The preliminary results showed that 4 out of 5 patients demonstrated reduction in the rate of cancer progression and an overall better quality of life as determined by patient reports of reduced pain, improved energy levels and increased appetite. The patients did not report any side effects related to the treatment with the softgels.

EXAMPLE 8

In Vivo Data—Reduction of Metastatic Tumour Volume in Human Patients

The purpose of this study was to evaluate the therapeutic benefit of a PAFP-atractyloside complex in treating solid tumours. The softgels were administered two caps daily, per os, one in the morning and one before bedtime, on an empty stomach in patients with metastatic disease.

Thirteen patients were evaluated. Twelve patients had been diagnosed with colon cancer and one patient with breast cancer. Each patient presented with metastatic disease, at least at one site. Seven patients were women and six were men, each ranging in age from 45 to 65.

Each patient was administered the PAFP-bound apoptosis-inducing agent (under the name CPA) at a dosage of 2 capsules (0.3 mg PAFP+0.006 mg of atractyloside per capsule) daily for 4 to 8 weeks. Computer tomography (CT) (Siemens, 16 layers) scans were performed before and after the treatment.

Following are the results of the study. Based on CT scan data, patient responses were classified as one of the following:
Full: No apparent metastasis
Partial: At least one metastasis has disappeared or is reduced in size
Stable: Metastasis growth within the World Health Organization standard for Stabilization (growth less than 25%).
Progression: Either an increase (more than 25%) in the size of metastasis or worsening of physical condition.
Interrupted: Side effects led to the interruption of the treatment.

Figure 6:
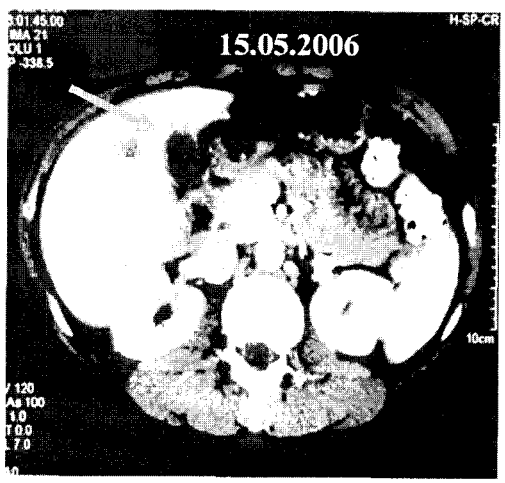
FIG. 6. Comparison of CT scans before (left) and after (right) 8 weeks of PAFP-atractyloside oral capsule treatment in cancer patient P. having metastatic adenocarcinoma of the colon showing elimination of liver metastasis.
Figure 6:
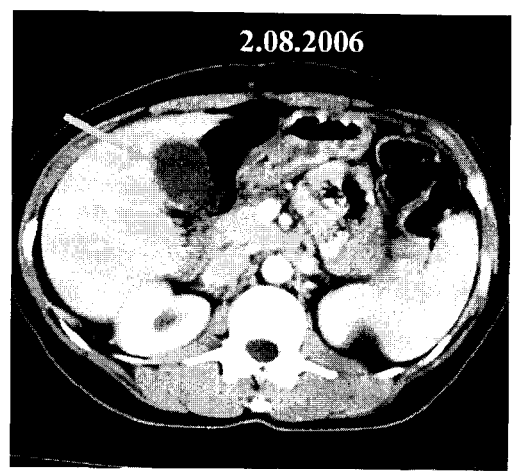
Figure 7:
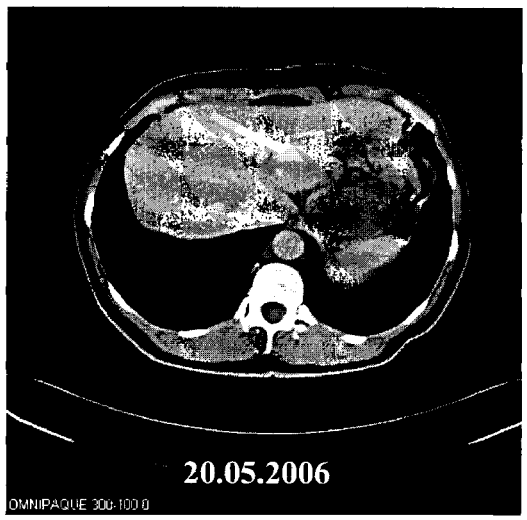
FIG. 7. Comparison of CT scans before (left) and after (right) 6 weeks of PAFP-atractyloside oral capsule treatment in cancer patient P.N.G. having metastatic adenocarcinoma of the colon showing elimination of liver metastasis.
Figure 7:
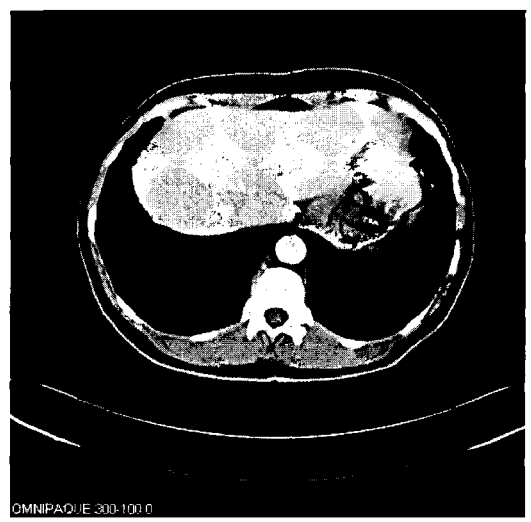

A summary of the patient data is provided in Table 4. CT scans taken before and after treatment are provided in FIGS. 6 and 7 for patients P. and P.N.G. each of whom demonstrated full response to the treatment.

TABLE 4

| Patient | Gender | Age (years) | Tumour | Previous Treatment | Response |
|---------|--------|-------------|--------|--------------------|----------|
| P | male | 56 | Colon adenocarcinoma | Tumour resection | full |
| P. N. G. | male | 62 | Colon adenocarcinoma | Tumour resection | full |
| A. N. A. | female | 48 | Colon adenocarcinoma | Chemotherapy | partial |
| A. N. P. | female | 63 | Colon adenocarcinoma | R. hemicolonectomy; chemotherapy | partial |
| S. V. A. | female | 45 | Colon adenocarcinoma | L. hemicolonectomy | partial |
| Z. T. P. | female | 49 | Breast carcinoma | Mastectomy; radiotherapy of regional lymph nodes | stable |
| G. N. K. | female | 62 | Colon adenocarcinoma | Tumour resection | stable |
| P. A. G. | male | 65 | Colon adenocarcinoma | Chemotherapy | stable |
| B. L. N. | female | 57 | Colon adenocarcinoma | Tumour resection | progression |
| K. A. R. | male | 52 | Colon adenocarcinoma | Chemotherapy | progression |
| K. V. I. | male | 48 | Colon adenocarcinoma | Chemotherapy | progression |
| P. A. V. | male | 65 | Colon adenocarcinoma | Tumour resection; chemotherapy | progression |
| R. D. P. | female | 62 | Colon adenocarcinoma | Tumour resection | interrupted |

Complete patient information is as follows:
Patient: P.
Gender: M. Age: 56 years old.
Clinical diagnosis: Colon Cancer (T2 N0 M0) Adenocarcinoma (B-123256-68 from 21 Jan. 2005)
Previous treatment: Surgery (Tumor resection)—15 Jan., 2005
Prior to Administration of PAFP-Atractyloside Composition:
May 2006—Progression: 1 Liver metastasis (Mts) (13×15 mm) (CT from May 15, 2006)
Administration of PAFP-atractyloside composition: 5 May 2006-15 Jul. 2006
The result of the treatment: NO Liver Mts (CT from 2 Aug. 2006)
Quality of life (Karnofsky Index)=80%
Side effects: None
Conclusion: Full response. Metastasis disappeared.
For Patient P., comparison of CT scans (FIG. 6) taken before treatment (left) and after treatment (right) shows that the metastasis (arrow) is no longer evident after treatment.
Patient: P.N.G.
Gender: M. Age: 62 years old.
Clinical diagnosis: Colon Cancer (T2 N0 M0). Adenocarcinoma (O-1045-48 from 1 Sep. 2005).
Previous treatment: Surgery (Tumor resection, Left)—August 2005

Prior to Administration of PAFP-Atractyloside Composition:
May 2006—Progression; 1 Liver Mts: 7×10 mm (CT from 20 May 2006)
  Quality of life (Karnofsky Index)=90%
Administration of PAFP-atractyloside composition: 10 Jun. 2006-22 Jul. 2006
The result of the treatment: NO Liver Mts (CT from 16 Aug. 2006)
  Quality of life (Karnofsky Index)=90%
  Side effects: None
Conclusion: Full response. Metastasis (7×10 mm) disappeared.

For patient P.N.G., a comparison of the CT scans (FIG. 7) taken before (left) and after (right) treatment shows that the metastasis (arrow) is no longer evident after treatment.

Patient: A.N.A.
Gender: F, Age: 48 years old.
Clinical diagnosis: Colon Cancer (T3a N1 M1), Metastasis:1 (Liver), Adenocarcinoma (B-1167-75 from 25 Sep. 2005)
Previous treatment: NO Surgery; Chemotherapy (Eloxatin, Alimta), October 2005-February 2006; Stabilization of the tumor growth
Prior to Administration of PAFP-Atractyloside Composition:
May 2006—Progression. Liver Mts (Left Lobe): 25×27 mm (CT from 28 May 2006)
  Quality of life (Karnofsky Index)=80%
Administration of PAFP-atractyloside composition: 10 Jun. 2006-12 Aug. 2006
The result of the treatment: Liver Mts (Left Lobe): 16×11 mm (CT from 21 Aug. 2006)
  Quality of life (Karnofsky Index)=90%
  Side effects: None
Conclusion: Partial response: Metastasis reduction.

The CT scans show 73% (25×27=675, 16×11=176, 675–176=499, 499/675=73.9%) reduction in size of a colon carcinoma metastasis in the liver of a patient who received twice daily doses of a PAFP-atractyloside composition.

Patient: A.N.P
Gender: F, Age: 63 years old
Clinical diagnosis: Colon Cr. (T3 N0 M0), Adenocarcinoma (O-1117-29 from 14 Jan. 2005)
Previous treatment: Surgery (Hemicolonectomy, right)—December 2004
August 2005—Progression. Chemotherapy—Eloxatin, Xeloda, 5-FU; Partial response
Prior to Administration of PAFP-Atractyloside Composition:
May 2006—Progression, Retzidiv: 3 Liver Mts: 21×28 mm, 27×29 mm, 10×12 mm (CT from 17 May 2006)
  Quality of life (Karnofsky Index)=70-80%
Administration of PAFP-atractyloside composition: 5 Jun. 2006-30 Jul. 2006
The result of the treatment: 2 Liver Mts: 21×28 mm, 27×29 mm (CT from 8 Aug. 2006)
  Quality of life (Karnofsky Index)=90%
  Side effects: None
Conclusion: Partial response: Disappearance of one (10×12 mm) of the liver metastases.

Patient: S.V.A.
Gender: F. Age: 45 years old
Clinical diagnosis: Colon Cancer (T2 N1 M0). Adenocarcinoma (O-1135-42 from 25 Mar. 2004)
Previous treatment: Surgery (Hemicolectomy, left)—March 2005
  May 2006—symptomatic therapy
Prior to Administration of PAFP-Atractyloside Composition:
April 2006—Progression: 3 Liver Mts: 45×65 mm, 26×42 mm and 7×9 mm (CT from 26 Apr. 2006)
  Quality of life (Karnofsky Index)=80%
Administration of PAFP-atractyloside composition: 29 Jun. 2006-24 Jul. 2006
The result of the treatment: 2 Liver Mts: 42×55 mm and 26×42 mm (CT from 3 Aug. 2006)
  Quality of life (Karnofsky Index)=90%
  Side effects: None
Conclusion: Partial response: 1 Metastasis eliminated (7×9 mm), 2 Metastases stabilized.

Patient: Z.T.P.
Gender: F. Age: 49 years old
Clinical diagnosis: Breast Cr. (T3b N1 M0)
Previous treatment: Surgery (Mastectomy)—December 2004; Radiotherapy (region of lymph nodes);
  Treatment by Taxotere; Stabilization
Prior to Administration of PAFP-Atractyloside Composition:
July 2006—Progression. 1 Liver Mts: 67×69 mm. (CT from 18 Jul. 2006)
  Quality of life (Karnofsky Index)=90%
Administration of PAFP-atractyloside composition: 5 Aug. 2006-2 Sep. 2006
The result of the treatment: 1 Liver Mts: 68×66 mm. (CT from 30 Aug. 2006)
  Quality of life (Karnofsky Index)=90%
  Side effects: None
Conclusion: Stabilization.

Patient: G.N.K.
Gender: F, Age: 62 years old
Clinical diagnosis: Colon Cancer (T2 N0 M0), Adenocarcinoma (O-1086-92 from 14 Jun. 2005)
Previous treatment: Surgery (Tumor resection, right)—June 2005
Prior to administration of PAFP-atractyloside composition:
June 2006—Progression: 2 Liver Mts: 8×6 mm and 6×6 mm (CT from 10 Jun. 2006)
  Quality of life (Karnofsky Index)=90%
Administration of PAFP-atractyloside composition: 1 Jul. 2006-2 Sep. 2006
The result of the treatment: 2 Liver Mts: 8×6 mm and 6×6 mm (CT from 15 Sep. 2006)
  Quality of life (Karnofsky Index)=90%
  Side effects: None
Conclusion: Stabilization.

Patient: P.A.G.
Gender: M. Age: 65 years old
Clinical diagnosis: Colon Cr. (T2 N0 M0). Adenocarcinoma (O-1256-65 from 25 Sep. 2005)
Previous treatment: Surgery operation—September 2005. December 2005—Progression; Mts In Liver
  5 courses of Chemotherapy: 5-FU.
Prior to Administration of PAFP-Atractyloside Composition:
June 2006—Progression: 2 Liver Mts: 32×24 mm and 32×26 mm (CT from 14 Jun. 2006)
  Quality of life (Karnofsky Index)=90%
Administration of PAFP-atractyloside composition: 19 Jun. 2006-13 Aug. 2006
The result of the treatment: 2 Liver Mts: 32×24 mm and 32×26 mm (CT from 22 Aug. 2006)
  Quality of life (Karnofsky Index)=90%
  Side effects: None
Conclusion: Stabilization Patient: B.L.N.
Gender: F, Age: 57 years old
Clinical diagnosis: Colon Cancer (T3b N0 M0), Adenocarcinoma (O-1245-61 from 14 Jan. 2006)
Previous treatment: Surgery (Tumor resection, right)—December 2005

Prior to Administration of PAFP-Atractyloside Composition:
June 2006—Progression: Liver Mts: 18×12 mm (CT from 19 Jun. 2006)
Quality of life (Karnofsky Index)=90%
Administration of PAFP-atractyloside composition: 2 Jul. 2006-27 Aug. 2006
The result of the treatment: Liver Mts: 22×18 mm (CT from 4 Sep. 2006)
Quality of life (Karnofsky Index)=90%
Side effects: None
Conclusion: Progression. Metastasis increased more than 25%.
Patient: K.A.R.
Gender: M. Age: 52 years old
Clinical diagnosis: Colon Cancer (T3b N1 M1-Hep.), Adenocarcinoma (B-1189-96)
Previous treatment: NO Surgery. Chemotherapy—Eloxatin (December 2005-February 2006).
Stabilization
Prior to Administration of PAFP-Atractyloside Composition:
June 2006—Progression: 1 Liver Mts: 118×85 mm (CT from 19 Jun. 2006)
Quality of life (Karnofsky Index)=60-70%
Administration of PAFP-atractyloside composition: 26 Jun. 2006-27 Aug. 2006
The result of the treatment: 1 Liver Mts: 18×85 mm (CT from 19 Jun. 2006)
Quality of life (Karnofsky Index)=40-50%
Temperature running in the evening. Cannot walk.
Side effects: Vomiting, nausea
Conclusion: Clinical progression. Metastasis—not dynamic (Stabilization)
Patient: K.V.I.
Gender: M, Age: 48 years old
Clinical diagnosis: Colon Cancer (T3b N1 M1-Hep.). Adenocarcinoma (B-1245-50)
Previous treatment: NO Surgery. Chemotherapy—Eloxatin (October-November 2005).
Partial Response
Prior to Administration of PAFP-Atractyloside Composition:
May 2006—Progression: 1 Liver Mts: 19×9 mm (CT from 16 May 2006)
Quality of life (Karnofsky Index)=90%
Administration of PAFP-atractyloside composition: 5 Jun. 2006-30 Jul. 2006
The result of the treatment: 1 Liver Mts: 28×32 mm (CT from 8 Aug. 2006)
Quality of life (Karnofsky Index)=90%
Side effects: None
Conclusion: Progression.
Patient: P.A.V.
Gender: M. Age: 65 years old
Clinical diagnosis: Colon Cr. (T3a N0 M0). Adenocarcinoma (O-1212-34 from 12 Feb. 2005).
Previous treatment: Surgery (tumor resection)—February 2005
October 2005—Progression; Mts in Liver
October-November 2005—Chemotherapy (Eloxatin)—Partial Response
Prior to Administration of PAFP-Atractyloside Composition:
June 2006—Progression. 2 Liver Mts: 7×8 mm and 5×6 mm (CT from 6 Jun. 2006)
Quality of life (Karnofsky Index)=90%.
Administration of PAFP-atractyloside composition: 5 Jun. 2006-6 Aug. 2006.
The result of the treatment: 2 Liver Mts: 12×9 mm and 6×8 mm (CT from 7 Aug. 2006)
Quality of life (Karnofsky Index)=90%
Side effects: None.
Conclusion: Progression.
Patient: R.D.P.
Gender: F. Age: 62 years old
Clinical diagnosis: Colon Cancer (T2 N1 M0). Adenocarcinoma (O-1187-48 from 29 Sep. 2004)
Previous treatment: Surgery (Tumor resection, left)—September 2004
Prior to Administration of PAFP-Atractyloside Composition:
May 2006—Progression: 2 Liver Mts: 65×85 mm and 46×22 mm, tend to fusion (CT from 14 May 2006)
Quality of life (Karnofsky Index)=90%
Administration of PAFP-atractyloside composition: June, 2006
The result of the treatment: not determined
Side effects: Vomiting, nausea; not inhibited by antiemetics
Conclusion: Treatment was interrupted because of side effect (vomiting, nausea)

Taking into consideration the advanced stage of cancer being treated in this study, the results of indicate that of the 13 patients who were administered daily doses of CPA, 61% (8/13) demonstrated a response. A response means that either the metastatic masses were undetectable after the treatment (15%, 2/13), that at least one metastatic mass was eliminated or reduced in size (23%, 3/13) or that no progression was observed in metastatic growth (stabilization, 23%, 3/13).

Four patients experienced progression of their disease (31%) and one (8%) was removed from the study due to side effects (vomiting, nausea). The main investigator could not determine if the side effects were directly related to the treatment and suggests that the size of the initial metastasis in the liver (65×85 mm and 46×22 mm, tendency to fusion) could have had an effect.

There were no serious adverse effects reported aside from one case of vomiting which could not be directly correlated to the intake of the product.

Patients A.N.A. and A.N.P. had multi-drug resistant metastases that developed after treatments with Eloxatin/Alimta, and Eloxatin/Xeloda/5-FU respectively. After PAFP-atractyloside composition treatment, these patients demonstrated reduction in metastatic tumour size. These data support the ability of the PAFP-atractyloside complex to overcome multi-drug resistance in vivo.

The foregoing are specific examples of certain aspects of the present invention. Many other embodiments, including modifications and variations thereof, are also possible and will become apparent to those skilled in the art upon a review of the invention as described herein. Accordingly, all suitable modifications, variations and equivalents may be resorted to, and such modifications, variations and equivalents are intended to fall within the scope of the invention as described herein and within the scope of the appended claims.

REFERENCES

Abelev, G. I., Alpha-fetoprotein: 25 years of study. *Tumor Biology*, 10:63-74; 1989.
Boik, John., Natural Compounds in Cancer Therapy, Promising Nontoxic Antitumor Agents from Plants & Other Animal Sources, Minnesota: Oregon Medical Press, 2001.
Bykov, V. J. et al., Restoration of the tumor suppressor function to mutant p53 by a low-molecular-weight compound. *Nat. Medicine* 8(3): 283-8, 2002.
Costantini et al., Mitochondrion as a novel target of anticancer chemotherapy. *J. Natl. Cancer Inst.* 92(13): 1042-53, 2000.

Decaudin D, Geley S, Hirsch T, et al., Bcl-2 and Bcl-XL antagonize the mitochondrial dysfunction preceding nuclear apoptosis induced by chemotherapeutic agents. *Cancer Res.* 1997; 57:62-67.

Dudich et al., Alpha-fetoprotein causes apoptosis in tumor cells via a pathway independent of CD95, TNFR1 and TNRF2 through activation of caspase-3-like proteases. *Eur. J. Biochem.* 266:1-13, 1999.

Evan, G. I. and Vousden, K. H., Proliferation, cell cycle and apoptosis in cancer. *Nature* 411:342-348, 2001.

Feldman, N. B. et al., Antitumor activity of AFP conjugate with doxorubicin in vitro and in vivo. *Biochemistry* 65:1140-1145, 2000.

Fisher, D. E., Apoptosis in cancer therapy: crossing the threshold. *Cell* 78: 539-542, 1994.

Fulda, S. et al., Activation of mitochondria and release of mitochondrial apoptogenic factors by betulinic acid. *J. Biol. Chem.* 18: 273 (51): 33942-8, 1998.

Germann U A., P-glycoprotein-a mediator of multidrug resistance in tumour cells. *Eur. J. Cancer,* 32A:927-944, 1996.

Hirano, K. et al., Drug-binding properties of human AFP. *Biochem. J.,* 231, 189-191, 1985.

Keel, B. A., Cho, S., Characterization of human AFP charge microheterogeneity by chromatofocusing, Mizejewski G I, Jacobson H I, eds., Biological Activities of Alpha1-Fetoprotein. Boca Raton, Fla.: CRC Press; vol 2, 24-31, 1989.

Kim et al., Mapping of the porcine alpha-fetoprotein (AFP) gene to swine chromosome 8. International Society for Animal Genetics, *Animal Genetics,* 33:468-485, 2002.

Kroemer, G., Zamzami, N., Susin, S. A., Mitochondrial control of apoptosis. *Immunol Today* 18: 44-51, 1997.

Laborda, J., Naval, J., Allouche, M., Calvo, M., Georgoulias, V., Mishal, Z., Uriel. J., Specific uptake of AFP by malignant human lymphoid cells. *Int. J. Cancer* 40:314-318, 1987.

Lehnert M., Clinical multidrug resistance in cancer: a multifactorial problem. *Eur. J. Cancer* 32A: 912-920, 1996.

Lutsenko et al., Antitumor Activity of Alpha Fetoprotein and Epidermal Growth Factor Conjugates in vitro and in vivo. *Tumor Biology* 21(6):367-374, 2000.

Marchetti, P., Castedo, M., Susin, S. A., Zamzami, N., Hirsch, T., Macho, A., Haefffer, A., Hirsch, F., Geuskens, M., and Kroemer, G. J., *Exp. Med.* 184, 1155-1160, 1996.

Mizejewski, G. J., Alpha-fetoprotein, Monographs on Endocrinology, Ulrich Westphal, Steroid-protein interactions II, Springer-Verlag, Berlin, New-York, Tokyo, 1986, 320-356.

Mizejewski, G. J. et al., Studies of the intrinsic antiuterotropic activity of murine alpha-fetoprotein. *Tumour Biol.* 7(1): 19-36, 1986.

Mizejewski, G. J., Alpha-fetoprotein structure and function relevance to isoforms, epitopes and conformational variants. *Exp. Biol. Med.* 226(5): 377-408, 2001.

Mizejewski, G. J., New insights into AFP structure and function: potential biomedical applications, Alpha-Fetoprotein and Congenital Disorders, ed. Mizejewski G. I., Academic Press, Inc., 1985.

Mizejewski G I, Jacobson H I, eds., Biological Activities of Alpha1-Fetoprotein. Boca Raton, Fla.: CRC Press; vol 1, 1987; vol 2, 1989.

Morinaga, T, Sakai, M, Wegmann, T G, Tamaoki, T., Primary structures of human alpha-fetoprotein and its mRNA. Proc. Natl. Acad. Sci. USA, 1983 August; 80(15):4604-8.

Moro, R., The AFP receptor—a widespread oncofetal antigen, Biological Activities of AFP, CRC Press, Boca Raton, Fla., vol. 2, 120-127, 1987.

Moro-Vidal, R., The AFP receptor: a widespread cancer marker of clinical potential, Curex technologies Inc., www.biocurex.com.

Moskaleva et al., Alpha-fetoprotein-mediated targeting: a new strategy to overcome multidrug resistance of tumour cells in vitro. *Cell Biol. Int.* 21(12):793-91997, 1997.

Murgita, R. A., Recombinant alpha-fetoprotein hybrid cytotoxins for treating and diagnosing cancers, U.S. Pat. No. 6,534,479, Mar. 18, 2003.

Murgita, R. A., Recombinant alpha-fetoprotein for treating cancers, U.S. Pat. No. 6,630,445 Oct. 7, 2003.

Nishi, S., Watabe, H., Hirai, H., Immunological and chemical correlation between AFPs from human and several mammalian species. *Ann. NY Acad. Sci.,* 259:109-118, 1975.

Nunez, E. A., Benassayag, C., Ballette, G., Martin M. E., Vranckx, R., Christeff, N., Garreau, B., The physiochemical and biological properties of AFP depend on its ligand environment. *J. Nucl. Med. Allied Sci.,* 33:18-16, 1989.

Pak, V. N. et al., Method of treatment of malignant neoplasms and complex preparation having antineoplastic activity for use in such treatment, U.S. Pat. No. 6,878,688, 2005.

Parker, M. H. et al., Purification and characterization of a recombinant version of human AFP expressed in the milk of transgenic goats. *Protein Expression and Purification,* 38:177-183, 2004.

Pessayre et al, Hepatocyte Apoptosis Trigged by Natural Substances, Apoptosis and Its Modulation by Drugs, eds. R. G. Cameron, G. Feuer, Springer Press, 86-108, 2000.

Pezzuto et al., Method of preparing and use of prodrugs or betulinic acid derivatives, US Patent Application Publication No. 2003/0186945.

Putt et al., Small molecule activation of procaspase-3 to caspase-3 as a personalized anticancer strategy. *Nature Chem. Biol.,* 2:543-550, 2006.

Ruoslahti, E., Seppala, M., Studies of carcino-fetal proteins. III. Development of radio-immunoassay for alpha-fetoprotein. Demonstration of alpha-fetoprotein in serum of healthy human adults. *Intl. J. Cancer* 8: 374-383, 1971.

Ruoslahti, E., Engvall, E., Pekkala, M., Seppala, M., Developmental changes in carbohydrate moiety of AFP. *Int. J. Cancer,* 22:515-520, 1978.

Severin, S. E. et al., Alpha-fetoprotein-mediated targeting of anti-cancer drugs to tumor cells in vitro. *Biochem. Mol. Biol. Int.* 37(2):385-92, 1995.

Severin, S. E. et al., Antitumor activity of a covalent conjugate of the endiene antibiotic esperamicin A1 with human alpha-fetoprotein. *Dokl. Akad. Nauk,* 366(4): 561-4, 1999.

Sotnichenko, A. I., Severin, S. E., Posypanova, G. A., Feldman, N. B., Grigor, M. I., Severin, E. S., Petrov, R. V., Water-soluble 2,3,7,8-tetrachlorodibenzo-p-dioxin complex with human AFP: properties, toxicity in vivo, and anti-tumor activity in vivo. *FEBS Lett.,* 450:49-51, 1999.

Susin, S. A., Zamzami, N., Castedo, M., Hirsch, T., Marchetti, P., Macho, A., Daugas, E., Geuskens, M., and Kroemer, G. *J. Exp. Med.,* 184, 1331-1341, 1996.

Thomas, H., Coley, H. M, Overcoming Multidrug Resistance in Cancer: An Update on the Clinical Strategy of Inhibiting P-Glycoprotein. *Cancer Control,* 10(2):159-165, 2003.

Torres, J. M., Geuskens, M., Uriel, J., Receptor-mediated endocytosis and recycling of AFP in human B-lymphoma and T-leukemia cells. *Int. J. Cancer,* 47:110-117, 1991.

Uriel et al., Biological activities of alpha-fetoprotein, Florida Congresses, ed. Mizejewski, G. J., CRC Press Inc., Boca Raton, Vol. 2, 104-117, 1987.

Wu, J. T., Clayton F., Detection of various isoforms of human AFP, Mizejewski G I, Jacobson H I, eds. Biological Activities of Alpha1-Fetoprotein. Boca Raton, Fla.: CRC Press; vol 2, 3-13, 1987.

Zamzani, N., Susin, S. A., Marchetti, P., Mitochondrial control of nuclear apoptosis. *J. Exp. Med.*, 183:1533-1544, 1996.

What is claimed is:

1. An oral dosage form comprising a composition comprising a non-covalent complex of:
   porcine alpha-fetoprotein (PAFP) prepared from raw material using butanol extraction; and
   at least one apoptosis-inducing agent selected from the group consisting of betulinic acid, atractyloside and thapsigargin,
   said at least one apoptosis-inducing agent being present in said composition in an amount of 150 μg or less,
   wherein the at least one apoptosis-inducing agent reversibly binds to the PAFP.

2. The oral dosage form according to claim 1, wherein two apoptosis-inducing agents that reversibly bind to the PAFP are present.

3. The oral dosage form according to claim 1, wherein the PAFP is prepared using the following process:
   (a) collecting blood and amniotic fluid from porcine embryos of from about 3 to about 14 weeks gestation;
   (b) separating the blood and the amniotic fluid collected in (a) into a supernatant and a precipitate;
   (c) collecting the supernatant resulting from (b);
   (d) concentrating the supernatant resulting from (c) to form a concentrated solution;
   (e) adding butanol to the concentrated solution of (d) to a final concentration of from about 5% to about 10% butanol in solution;
   (f) stirring the butanol solution resulting from (e);
   (g) separating the butanol solution resulting from (f) into an upper non-aqueous phase and a lower aqueous phase; and
   (h) collecting the non-aqueous phase resulting from (g) to produce a final solution containing PAFP.

4. The oral dosage form according to claim 1, wherein the PAFP is prepared from porcine embryos of from about 3 to about 14 weeks gestation.

5. The oral dosage form according to claim 1 wherein the at least one apoptosis-inducing agent is betulinic acid.

6. The oral dosage form according to claim 1 wherein the at least one apoptosis-inducing agent is atractyloside.

7. The oral dosage form according to claim 1 wherein the PAFP of said composition specifically binds to cells having at least one AFP receptor on the cell surface.

8. The oral dosage form according to claim 1 wherein said oral dosage form is in the form of a capsule, softgel or tablet.

9. A method for targeted delivery in a patient of at least one apoptosis-inducing agent to a cancer cell having at least one AFP receptor on a cell surface, said method comprising administering to said patient the oral dosage form according to claim 1, wherein the at least one apoptosis-inducing agent reversibly binds to the PAFP, and the PAFP specifically binds to the at least one AFP receptor.

10. The method according to claim 9, wherein the PAFP is prepared using the following process:
   (a) collecting blood and amniotic fluid from porcine embryos of from about 3 to about 14 weeks gestation;
   (b) separating the blood and the amniotic fluid collected in (a) into a supernatant and a precipitate;
   (c) collecting the supernatant resulting from (b);
   (d) concentrating the supernatant resulting from (c) to form a concentrated solution;
   (e) adding butanol to the concentrated solution of (d) to a final concentration of from about 5% to about 10% butanol in solution;
   (f) stirring the butanol solution resulting from (e);
   (g) separating the butanol solution resulting from (f) into an upper non-aqueous phase and a lower aqueous phase; and
   (h) collecting the non-aqueous phase resulting from (g) to produce a final solution containing PAFP.

11. A method for inhibition of proliferation of a cancer cell in a patient, said cancer cell having at least one AFP receptor on a cell surface, said method comprising administering to said patient the oral dosage form according to claim 1, wherein the at least one apoptosis-inducing agent reversibly binds to the PAFP, and the PAFP specifically binds to the at least one AFP receptor on the cell surface.

12. The method according to claim 11, wherein the cancer is selected from the group consisting of bladder cancer, breast cancer, colon and rectal cancer, endometrial cancer, kidney cancer, leukemia, liver cancer, lung cancer, melanoma, non-Hodgkin's lymphoma, ovarian cancer, pancreatic cancer, prostate cancer, skin cancer, testicular cancer and thyroid cancer.

13. The method according to claim 11, wherein the PAFP is prepared using the following process:
   (a) collecting blood and amniotic fluid from porcine embryos of from about 3 to about 14 weeks gestation;
   (b) separating the blood and the amniotic fluid collected in (a) into a supernatant and a precipitate;
   (c) collecting the supernatant resulting from (b);
   (d) concentrating the supernatant resulting from (c) to form a concentrated solution;
   (e) adding butanol to the concentrated solution of (d) to a final concentration of from about 5% to about 10% butanol in solution;
   (f) stirring the butanol solution resulting from (e);
   (g) separating the butanol solution resulting from (f) into an upper non-aqueous phase and a lower aqueous phase; and
   (h) collecting the non-aqueous phase resulting from (g) to produce a final solution containing PAFP.

14. A method for treating multidrug resistance in refractory malignant neoplasms in a patient, said refractory malignant neoplasms being comprised of cancer cells having at least one AFP receptor on a cell surface, said method comprising administering to said patient a the oral dosage form according to claim 1, wherein the at least one apoptosis-inducing agent reversibly binds to the PAFP, and the PAFP specifically binds to the at least one AFP receptor on the cell surface.

15. The method according to claim 14, wherein the cancer is selected from the group consisting of bladder cancer, breast cancer, colon and rectal cancer, endometrial cancer, kidney cancer, leukemia, liver cancer, lung cancer, melanoma, non-Hodgkin's lymphoma, ovarian cancer, pancreatic cancer, prostate cancer, skin cancer, testicular cancer and thyroid cancer.

16. The method according to claim 14, wherein the PAFP is prepared using the following process:
   (a) collecting blood and amniotic fluid from porcine embryos of from about 3 to about 14 weeks gestation;
   (b) separating the blood and the amniotic fluid collected in (a) into a supernatant and a precipitate;
   (c) collecting the supernatant resulting from (b);
   (d) concentrating the supernatant resulting from (c) to form a concentrated solution;

(e) adding butanol to the concentrated solution of (d) to a final concentration of from about 5% to about 10% butanol in solution;
(f) stirring the butanol solution resulting from (e);
(g) separating the butanol solution resulting from (f) into an upper non-aqueous phase and a lower aqueous phase; and
(h) collecting the non-aqueous phase resulting from (g) to produce a final solution containing PAFP.

17. The oral dosage form as claimed in claim 1, wherein said composition exhibits efficient gastrointestinal absorption after oral administration.

18. The oral dosage form as claimed in claim 1, wherein said at least one apoptosis-inducing agent is atractyloside, and said atractyloside is present in said composition in an amount of 6 µg.

19. The oral dosage form as claimed in claim 1, wherein said at least one apoptosis-inducing agent is betulinic acid, and said betulinic acid is present in said composition in an amount of 6 µg to 8 µg.

20. An oral dosage form comprising a composition comprising:
    a non-covalent complex of:
        porcine alpha-fetoprotein (PAFP) prepared from raw material using butanol extraction; and
        betulinic acid in an amount of 6 µg to 8 µg;
    and, optionally, additional betulinic acid in an amount of 150 µg, wherein said additional betulinic acid is not in complex with said PAFP;
    wherein said betulinic acid reversibly binds to the PAFP.

21. A method for delivering at least one apoptosis-inducing agent to a cancer cell in a patient, said cancer cell having at least one alpha-fetoprotein (AFP) receptor on a cell surface, wherein said at least one apoptosis-inducing agent is selected from the group consisting of betulinic acid, atractyloside, and thapsigargin, said method comprising binding the at least one apoptosis-inducing agent reversibly to a PAFP prepared from raw material using butanol extraction to form a non-covalent complex, and orally administering a dosage form comprising a composition comprising said non-covalent complex to said patient, wherein the PAFP binds specifically to the at least one AFP receptor, and said at least one apoptosis-inducing agent is present in said composition in an amount of 150 µg or less.

22. The method according to claim 21, wherein the PAFP is prepared using the following process:
    (a) collecting blood and amniotic fluid from porcine embryos of from about 3 to about 14 weeks gestation;
    (b) separating the blood and the amniotic fluid collected in (a) into a supernatant and a precipitate;
    (c) collecting the supernatant resulting from (b);
    (d) concentrating the supernatant resulting from (c) to form a concentrated solution;
    (e) adding butanol to the concentrated solution of (d) to a final concentration of from about 5% to about 10% butanol in solution;
    (f) stirring the butanol solution resulting from (e);
    (g) separating the butanol solution resulting from (f) into an upper non-aqueous phase and a lower aqueous phase; and
    (h) collecting the non-aqueous phase resulting from (g) to produce a final solution containing PAFP.

23. The oral dosage form according to claim 1 wherein the at least one apoptosis-inducing agent is thapsigargin.

* * * * *